(12) United States Patent
Kahook et al.

(10) Patent No.: US 11,857,461 B2
(45) Date of Patent: Jan. 2, 2024

(54) LACRIMAL SYSTEM FOR DRUG DELIVERY

(71) Applicant: THE REGENTS OF THE UNIVERSITY OF COLORADO, Denver, CO (US)

(72) Inventors: Malik Y. Kahook, Denver, CO (US); Andrew Schieber, Laguna Niguel, CA (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 77 days.

(21) Appl. No.: 15/778,533

(22) PCT Filed: Nov. 16, 2016

(86) PCT No.: PCT/US2016/062201
§ 371 (c)(1),
(2) Date: May 23, 2018

(87) PCT Pub. No.: WO2017/091404
PCT Pub. Date: Jun. 1, 2017

(65) Prior Publication Data
US 2018/0344524 A1    Dec. 6, 2018

Related U.S. Application Data

(60) Provisional application No. 62/258,914, filed on Nov. 23, 2015.

(51) Int. Cl.
*A61F 9/007* (2006.01)
*A61F 9/00* (2006.01)
(Continued)

(52) U.S. Cl.
CPC ........ *A61F 9/00772* (2013.01); *A61F 9/0017* (2013.01); *A61M 37/00* (2013.01); *A61M 31/002* (2013.01)

(58) Field of Classification Search
CPC ... A61F 9/00772; A61F 9/0017; A61M 37/00; A61M 31/002
See application file for complete search history.

(56) References Cited

U.S. PATENT DOCUMENTS 3,817,248 A   6/1974 Buckles
3,828,777 A   8/1974 Ness
(Continued)

FOREIGN PATENT DOCUMENTS

CA    2829533 A1   8/2006
CN  201469516 U   5/2010
(Continued)

OTHER PUBLICATIONS

PCT International Search Report for PCT International Patent Application No. PCT/US2016/062201, dated Jan. 23, 2017.
(Continued)

*Primary Examiner* — Jessica Arble
(74) *Attorney, Agent, or Firm* — Polsinelli PC

(57) ABSTRACT

This invention is in the field of medical intervention related to the lacrimal system. The invention relates to a lacrimal system device or system and methods of using the device for drug delivery to the eye, sinuses and/or periocular tissues.

22 Claims, 15 Drawing Sheets

(51) Int. Cl.
*A61M 37/00* (2006.01)
*A61M 31/00* (2006.01)

(56) References Cited

U.S. PATENT DOCUMENTS

| | | | |
|---|---|---|---|
| 3,962,414 | A | 6/1976 | Michaels |
| 4,468,816 | A | 9/1984 | Kaufer |
| 4,658,816 | A | 4/1987 | Ector, Jr. |
| 4,781,675 | A | 11/1988 | White |
| 5,219,334 | A | 6/1993 | Tsukada |
| 5,318,513 | A | 6/1994 | Leib et al. |
| 5,410,016 | A | 4/1995 | Hubbell et al. |
| 5,437,625 | A | 8/1995 | Kurihashi |
| 5,836,935 | A | 11/1998 | Ashton et al. |
| 6,152,916 | A | 11/2000 | Bige |
| 6,196,993 | B1 * | 3/2001 | Cohan ............ A61F 9/0017 604/891.1 |
| 6,217,896 | B1 * | 4/2001 | Benjamin ........ A61F 9/0017 424/420 |
| 6,344,047 | B1 * | 2/2002 | Price ............. A61F 9/00772 604/298 |
| 6,881,198 | B2 | 4/2005 | Brown |
| 7,066,904 | B2 | 6/2006 | Rosenthal et al. |
| 8,034,370 | B2 | 10/2011 | Shiah et al. |
| 8,409,606 | B2 | 4/2013 | Sawhney et al. |
| 8,563,027 | B2 | 10/2013 | Jarrett et al. |
| 2003/0014036 | A1 * | 1/2003 | Varner ........... A61M 31/002 604/521 |
| 2003/0114791 | A1 | 6/2003 | Rosenthal et al. |
| 2007/0298075 | A1 | 12/2007 | Borgia et al. |
| 2008/0086101 | A1 * | 4/2008 | Freilich ......... A61F 9/0017 604/294 |
| 2008/0181930 | A1 | 7/2008 | Rodstrom et al. |
| 2008/0199510 | A1 * | 8/2008 | Ruane ............ B82Y 30/00 424/426 |
| 2009/0104243 | A1 * | 4/2009 | Utkhede ......... A61F 9/0017 424/423 |
| 2009/0187098 | A1 * | 7/2009 | Makower ....... A61B 17/12022 600/424 |
| 2009/0306608 | A1 | 12/2009 | Li et al. |
| 2010/0034870 | A1 | 2/2010 | Sim et al. |
| 2010/0179468 | A1 | 7/2010 | Becker |
| 2010/0274204 | A1 * | 10/2010 | Rapacki ......... A61F 9/00772 604/285 |
| 2011/0251568 | A1 | 10/2011 | Beeley et al. |
| 2011/0301555 | A1 | 12/2011 | Gonzalez-Zugasti et al. |
| 2011/0311606 | A1 | 12/2011 | Coldren |
| 2011/0311607 | A1 | 12/2011 | Coldren |
| 2012/0095439 | A1 | 4/2012 | De Juan, Jr. et al. |
| 2013/0023837 | A1 | 1/2013 | Becker |
| 2013/0172268 | A1 | 7/2013 | Jarrett et al. |
| 2013/0220346 | A1 * | 8/2013 | Lust ............. A61F 9/00772 128/887 |
| 2013/0289467 | A1 * | 10/2013 | Haffner ......... A61F 9/00781 604/290 |
| 2014/0296834 | A1 * | 10/2014 | Moss ............. A61K 9/0036 604/515 |
| 2014/0364891 | A1 | 12/2014 | Mendius et al. |
| 2015/0351961 | A1 | 12/2015 | Kahook |
| 2019/0274877 | A1 | 9/2019 | Schieber et al. |

FOREIGN PATENT DOCUMENTS

| | | | | |
|---|---|---|---|---|
| CN | 201469516 | U | 5/2010 | |
| EP | 1891942 | | 3/2010 | |
| JP | 2006525953 | A | 11/2006 | |
| JP | 2012046530 | A | 3/2012 | |
| JP | 2012515628 | A | 7/2012 | |
| TW | 201212962 | A | 4/2012 | |
| WO | 0071062 | A1 | 11/2000 | |
| WO | 02056863 | | 7/2002 | |
| WO | 2004/062649 | A2 | 7/2004 | |
| WO | 2006/122165 | A2 | 11/2006 | |
| WO | 2008024982 | A2 | 2/2008 | |
| WO | 2008/043905 | A2 | 4/2008 | |
| WO | 2009032328 | A1 | 3/2009 | |
| WO | 2010/085696 | A2 | 7/2010 | |
| WO | 2014113384 | A2 | 7/2014 | |
| WO | WO-2014113384 | A2 * | 7/2014 | ......... A61K 9/0048 |

OTHER PUBLICATIONS

Fleisher et al., "Improved oral drug delivery: solubility limitations overcome by the use of prodrugs", Advanced Drug Delivery Reviews, 1996, vol. 19, No. 2, pp. 115-130.

Mooberry et al., "Tubercidin stabilizes microtubules against vinblastine-induced depolymerization, a taxol-like effect", Dancer Letters, 1995, vol. 96, No. 2, pp. 261-266.

Murube et al., "Subcutaneous abdominal artificial tears pump-reservoir for severe dry eyes," Orbit, 2003, vol. 22, No. 1, p. 29.

Ro et al., "Morphological and degradation studies of sirolimus-containing poly(lactide-co-glycolide) discs," Journal of Biomedical Materials Research Part B: Applied Biomaterials, 2012, vol. 100B, No. 3, pp. 767-777.

Smith et al., "A sensitive assay for taxol and other microtubule-stabilizing agents," Cancer Letters, 1994, vol. 79, No. 2, pp. 213-219.

* cited by examiner

LACRIMAL SYSTEM FOR DRUG DELIVERY

CROSS-REFERENCE TO RELATED APPLICATIONS

The present application claims the benefit of U.S. Provisional Patent Application No. 62/258,914, filed on Nov. 23, 2015, which is incorporated herein by reference.

FIELD OF THE INVENTION

This invention is in the field of medical intervention related to the lacrimal system. The invention relates to a lacrimal system device and methods of using the device for drug delivery to the eye, sinuses and/or periocular tissues.

BACKGROUND OF THE INVENTION

A variety of challenges face patients and physicians in the area of ocular and respiration disease or disorder management, including adequate drug delivery to the eyes or nasal passage and treatment of dry eyes. In ocular management, for example, many current ocular drug delivery systems require repetitive manual drug administration and are often ineffective due to a lack of patient compliance or inadequate drug concentrations reaching the eye. Many current tear flow blockage techniques also have drawbacks, including being irreversible in nature.

A previously used approach of drug delivery to an eye or periocular tissues can be to place a removable, drug-releasing punctal implant into a punctum. It is believed that by allowing for the sustained release of one or more drugs, the present punctal implants can overcome some of the drawbacks associated with current drug administration (i.e., manual drop instillation), such as poor patient compliance, waste, untimely application, or non-localized delivery. One approach to blocking of tear flow from the eye is to place a removable, but retainable, punctal implant into the punctum, commonly called punctal plugs. Such punctal plugs have been suggested to provide an avenue for extended release drug delivery, however they suffer from several drawbacks including: dislodgement and displacement (especially if a patient rubs the eye or lid too vigorously or sneezes), limited medication reservoir capacity, and uneven delivery of therapeutic agents in patients with poor tear production as agent dispersal is dependent upon distribution via dilution in available tears on the tear film of the eye. What is needed is a device that can supply long term, steady release of therapeutic agents to treat subjects in need of delivering active agents to the eye and/or periocular tissues.

SUMMARY OF THE INVENTION

This invention is in the field of medical intervention related to the lacrimal system. The invention relates to a lacrimal system and devices and methods of using the device for drug delivery to the eye, sinuses and/or periocular tissues.

In one embodiment, the invention relates to a lacrimal system for drug delivery, comprising: a) a reservoir balloon having an exit port; b) a tube comprising at least one lumen fluidly coupled to said exit port; c) an endcap comprising a port fluidly coupled to said tube; and d) a plug, the plug residing within the lumen of said tube. In one embodiment, said system further comprises a lubricant. In one embodiment, said system further comprises a guide-wire attached to said plug. In one embodiment, said system further comprises a guide-wire to enable delivery of said system into the lacrimal system. In one embodiment, said guide-wire is threaded through a lumen. In one embodiment, said system further comprises a guide-wire attached to said plug. In one embodiment, said reservoir balloon further comprises a fluid comprising a composition with an active ingredient. In one embodiment, said system further comprises at least one egress track connecting said endcap to outside of said reservoir balloon. In one embodiment, said egress track is designed to allow tears to flow from the ocular surface into the lacrimal sac and beyond. In one embodiment, said plug occludes a lumen. In one embodiment, said plug comprises silicone hydrogel. In one embodiment, the plug is a non-silicone hydrogel plug. In one embodiment, the plug may be selected from the group comprising nano-spheres, micro-spheres, filter membranes, porous membranes, porous materials such as foams and solid materials such as polymers with textured outer surfaces that will allow fluid to flow around etc. In one embodiment, the plug comprises materials with grooves. In one embodiment, said grooves are flow limiting tortuous paths for flow. In one embodiment, said plug comprises wicking material. In one embodiment, said plug controls the rate of flow of fluid from said reservoir balloon to said endcap. In one embodiment, said plug extends beyond the surface of said endcap. In one embodiment, said plug extends 1-200 microns beyond the surface of said endcap. In one embodiment, said tube is flexible. In one embodiment, the plug spans the distance from just beyond the endcap to the reservoir balloon. In one embodiment, the plug may occupy anywhere between $1/32$ to the full distance between the endcap and the reservoir balloon. In one embodiment, the tube comprises medical grade silicone. In one embodiment, the system does not have a tube, but rather only comprises a plug spanning the distance between the endcap to the reservoir balloon. In one embodiment, the plug comprises a flow-limiting rod. In one embodiment, said plug is colorless. In one embodiment, said plug is colored. In one embodiment, said plug comprises at least one fluorescent chemical compound. In one embodiment, said at least one fluorescent chemical compound fluoresces after exposure to a specific wavelength of light. In one embodiment, said reservoir balloon enables anatomical fixation. In one embodiment, fixation is achieved by the balloon inflating beyond the diameter of the proximal common canaliculus thus preventing it from extruding back into the proximal lacrimal outflow system. In one embodiment, said anatomical fixation is a system retention feature. In one embodiment, the system further comprises a secondary guide-wire extends the external length of said system. In one embodiment, the system further comprises a stiff but flexible 'under-wire' that gives the reservoir balloon a bracing structure. In one embodiment, the inflation system connects proximal to the endcap. In one embodiment, the reservoir balloon is substantially elastic. In one embodiment, the reservoir balloon is semi-elastic. In one embodiment, the reservoir balloon is substantially nonelastic. In one embodiment, said system is made of medical grade materials. In one embodiment, said tube comprises multiple lumens such that the plug (hydrogel), guide-wire or inflation lumens are each separate lumens. In the preferred embodiment, all three (the hydrogel plug, the guide wire, and the reservoir balloon inflation lumen) utilize the same lumen. In one embodiment, the hydrogel/plug is delivered through the inflation lumen. In one embodiment, said hydrogel plug is tethered to the bottom (distal part) of the reservoir balloon so that expansion of the balloon is limited in the long access and drives expansion of the balloon to the sides instead.

In one embodiment, the invention relates to a lacrimal system for drug delivery, comprising: a) a reservoir balloon having an exit port; b) a plug fluidly coupled to said exit port; and c) an endcap comprising a port fluidly coupled to said plug. In one embodiment, said system further comprises a guide-wire attached to said plug. In one embodiment, said reservoir balloon further comprises a fluid comprising a composition with an active ingredient. In one embodiment, said system further comprises at least one egress track connecting said endcap to outside of said reservoir balloon In one embodiment, said plug comprises silicone hydrogel. In one embodiment, said plug comprises wicking material. In one embodiment, said plug controls the rate of flow of fluid from said reservoir balloon to said endcap. In one embodiment, said plug extends beyond the surface of said endcap. In one embodiment, said plug extends 1-200 microns beyond the surface of said endcap. In one embodiment, said plug is flexible In one embodiment, said plug is colorless. In one embodiment, said plug is colored. In one embodiment, said plug comprises at least one fluorescent chemical compound. In one embodiment, said at least one fluorescent chemical compound fluoresces after exposure to a specific wavelength of light. In one embodiment, said reservoir balloon enables anatomical fixation In one embodiment, said anatomical fixation is a system retention feature. In one embodiment, said system is made of medical grade materials. In one embodiment, said system further comprises a lubricant. In one embodiment, said system further comprises a guide-wire to enable delivery of said system into the lacrimal system. In one embodiment, filling comprises introduction of said composition with at least one active ingredient through said tube. In one embodiment, said system further comprises a guide-wire attached to said plug, wherein said plug obtains a final position spanning the distance between said endcap and said reservoir balloon of said system. In one embodiment, said system further comprises at least one egress track connecting said endcap to outside of said reservoir balloon. In one embodiment, said egress track is designed to allow tears to flow from the ocular surface into the lacrimal sac and beyond. In one embodiment, said plug regulates the flow of said composition from said system. In one embodiment, said plug positioning within said lumen regulates the flow of said composition from said system. In one embodiment, said reservoir balloon enables anatomical fixation. In one embodiment, fixation is achieved by the balloon inflating beyond the diameter of the proximal common canaliculus thus preventing it from extruding back into the proximal lacrimal outflow system. In one embodiment, said anatomical fixation is a system retention feature. In one embodiment, the system further comprises a secondary guide-wire extends the external length of said system. In one embodiment, the system further comprises a stiff but flexible 'under-wire' that gives the reservoir balloon a bracing structure. In one embodiment, the inflation system connects proximal to the endcap. In one embodiment, the reservoir balloon is substantially elastic. In one embodiment, the reservoir balloon is semi-elastic. In one embodiment, the reservoir balloon is substantially nonelastic. In one embodiment, said system is made of medical grade materials. In one embodiment, the hydrogel/plug is attached to said guide-wire. In one embodiment, said hydrogel plug is tethered to the bottom (distal part) of the reservoir balloon so that expansion of the balloon is limited in the long access and drives expansion of the balloon to the sides instead.

In one embodiment, the invention relates to a method of treatment, comprising: a) providing: i) a subject comprising a punctum, lacrimal ducts, and a lacrimal sac, ii) a lacrimal drug delivery system, comprising: A) a reservoir balloon having an exit port, wherein said reservoir balloon is capable of insertion inside said lacrimal sac, B) a tube comprising at least one lumen fluidly coupled to said exit port, wherein said tube extends from said elastic reservoir through at least one of the lacrimal ducts, C) an endcap comprising a port fluidly coupled to the terminal end of said tube wherein said endcap interfaces with said punctum in contact with the tear film of the eye, and D) a plug, wherein the plug resides within the lumen of said tube of the system, and b) inserting said drug delivery system into said lacrimal system; c) filling said reservoir balloon with composition with at least one active ingredient; and d) administering said composition to said subject using said lacrimal system drug delivery system. In one embodiment, said system further comprises a guide-wire attached to said plug. In one embodiment, said composition with at least one active ingredient further comprises a therapeutic agent. In one embodiment, filling comprises introduction of said composition with at least one active ingredient through said tube. In one embodiment, step c) further comprises removal of said guide-wire attached to said plug, wherein said plug obtains a final position within the lumen of said system up until the endcap of said system. In one embodiment, said system further comprises at least one egress track connecting said endcap to outside of said reservoir balloon. In one embodiment, said egress track is designed to allow tears to flow from the ocular surface into the lacrimal sac and beyond. In one embodiment, said plug regulates the flow of said composition from said system. In one embodiment, said plug positioning within said lumen regulates the flow of said composition from said system. In one embodiment, the plug spans the distance from just beyond the endcap to the reservoir balloon. In one embodiment, the plug may occupy anywhere between ⅓₂ to the full distance between the endcap and the reservoir balloon. In one embodiment, the tube comprises medical grade silicone. In one embodiment, the system does not have a tube, but rather only comprises a plug spanning the distance between the endcap to the reservoir balloon. In one embodiment, the plug comprises a flow-limiting rod. In one embodiment, said guide-wire comprises a central open lumen. In one embodiment, said guide-wire is occupies a lumen of said system for delivery of said system into position. In one embodiment, said central open lumen is flexible. In one embodiment, said central open lumen allows injection of fluid distal directly into the balloon reservoir. In another embodiment, the delivery system is enhanced by internal characteristics of the system. In one embodiment, the system comprises a secondary guide-wire extends the external length of said system. In one embodiment, the system further comprises a stiff but flexible 'under-wire' that gives the reservoir balloon bracing structure. In one embodiment, the inflation system connects proximal to the endcap. In one embodiment, the reservoir balloon is substantially elastic. In one embodiment, the reservoir balloon is semi-elastic. In one embodiment, the reservoir balloon is substantially nonelastic. In some embodiments, the system comprises a protective sleeve be placed over said reservoir balloon. In one embodiment, said sleeve protects against leaks entering the nasal duct or other tissue compartments. In one embodiment, said system contains fluorescent material or coloring to allow for detection and position confirmation by the user (physician or patient). In one embodiment, the method further comprises filling said reservoir balloon with a therapeutic agent or medication. In one embodiment, said reservoir balloon is implanted within the sinuses surrounding the eye. In one embodiment, the punctal portion or endcap allows for filling the reservoir balloon with medication, but the reservoir balloon sits in a sinus and allows for delivery of drug through the plug to the tear film of the eye. In one embodiment, expansion of said balloon reservoir is at least 500%. In one embodiment, expansion of said balloon reservoir is at least 700%. In one embodiment, such the volume of said inflated balloon reservoir is at least 100 micro liters. There are not many types of balloons that could do this. In one embodiment, said balloon reservoir comprises silicone. In one embodiment, said reservoir balloon enables anatomical fixation. In one embodiment, fixation is achieved by the balloon inflating beyond the diameter of the proximal common canaliculus thus preventing it from extruding back into the proximal lacrimal outflow system. In one embodiment, said anatomical fixation is a system retention feature. In one embodiment, said plug regulates the flow of said composition from said system. In one embodiment, said plug positioning within said lumen regulates the flow of said composition from said system. In one embodiment, said active ingredient consists of artificial tears, glaucoma drops, anti-inflammatory agents, nonsteroidal agents, antibiotics, biologics, proteins, aptamers, nucleic acids, cytokines, plasma, sympahtomemetics, parasympathomemetics, prostaglandin analogues, beta blockers, alpha-agonists, and anti-VEGF agents. In one embodiment, the flow of said fluid out of said system is controlled by adjustment of said plug by an operator (patient or physician) to decrease flow at given times of the day when treatment might not be needed (while sleeping for example). In one embodiment, the reservoir balloon will deliver fluid+/−active ingredients to the ocular surface at a fixed rate between 0.1 micro liters and 30.0 micro liters per day for a minimum of one week. In another embodiment, the delivery is achieved for a minimum of 60 days.

In one embodiment, the invention relates to a method of treatment, comprising: a) providing: i) a subject comprising a punctum, lacrimal ducts, and a lacrimal sac, ii) a lacrimal drug delivery system, comprising: A) a reservoir balloon having an exit port, comprising a composition with at least one active ingredient, wherein said reservoir is capable of insertion inside said lacrimal sac, B) a tube comprising a lumen connected to said exit port extending from said elastic reservoir through at least one of the lacrimal ducts, C) a endcap comprising a port connected to the terminal end of said tube wherein said endcap interfaces with said punctum in contact with the tear film of the eye, and D) a plug, wherein the plug resides within the lumen of said tube of the system, b) inserting said drug delivery system into said lacrimal system; and c) administering said composition to said subject using said lacrimal system drug delivery system. In one embodiment, said system further comprises a lubricant. In one embodiment, said system further comprises a guide-wire to enable delivery of said system into the lacrimal system. In one embodiment, said system further comprises a guide-wire attached to said plug. In one embodiment, said guide-wire comprises a central open lumen. In one embodiment, said central open lumen is flexible. In one embodiment, said central open lumen allows injection of fluid distal directly into the balloon reservoir. In another embodiment, the delivery system is enhanced by internal characteristics of the system. No secondary guide-wire is needed to travel the length since there is a stiff but flexible 'under-wire' that gives the plug some push-ability. In this embodiment, the inflation system connects proximal to the endcap. In one embodiment, said system further comprises at least one egress track connecting said endcap to outside of said reservoir balloon. In one embodiment, said egress track is designed to allow tears to flow from the ocular surface into the lacrimal sac and beyond. In one embodiment, the reservoir balloon is substantially elastic. In one embodiment, the reservoir balloon is semi-elastic. In one embodiment, the reservoir balloon is substantially nonelastic. In some embodiments, the system comprises a protective sleeve be placed over said reservoir balloon. In one embodiment, said sleeve protects against leaks entering the nasal duct or other tissue compartments. In one embodiment, said system contains fluorescent material or coloring to allow for detection and position confirmation by the user (physician or patient). In one embodiment, the method further comprises filling said reservoir balloon with a therapeutic agent or medication. In one embodiment, said reservoir balloon is implanted within the sinuses surrounding the eye. In one embodiment, the punctal portion or endcap allows for filling the reservoir balloon with medication, but the reservoir balloon sits in a sinus and allows for delivery of drug through the plug to the tear film of the eye. In one embodiment, expansion of said balloon reservoir is at least 500%. In one embodiment, expansion of said balloon reservoir is at least 700%. In one embodiment, such the volume of said inflated balloon reservoir is at least 100 micro liters. In one embodiment, said balloon reservoir comprises silicone. In one embodiment, said reservoir balloon enables anatomical fixation. In one embodiment, fixation is achieved by the balloon inflating beyond the diameter of the proximal common canaliculus thus preventing it from extruding back into the proximal lacrimal outflow system. In one embodiment, said anatomical fixation is a system retention feature. In one embodiment, said plug regulates the flow of said composition from said system. In one embodiment, said plug positions within said lumen regulates the flow of said composition from said system. In one embodiment, said active ingredient consists of artificial tears, glaucoma drops, anti-inflammatory agents, nonsteroidal agents, antibiotics, biologics, proteins, aptamers, nucleic acids, cytokines, plasma, sympahtomemetics, parasympathomemetics, prostaglandin analogues, beta blockers, alpha-agonists, and anti-VEGF agents. In one embodiment, the flow of said fluid out of said system is controlled by adjustment of said plug by an operator (patient or physician) to decrease flow at given times of the day when treatment might not be needed (while sleeping for example). In one embodiment, the reservoir balloon will deliver fluid+/−active ingredients to the ocular surface at a fixed rate between 0.1 micro liters and 30.0 micro liters per day for a minimum of one week. In another embodiment, the delivery is achieved for a minimum of 60 days.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "patient" or "subject" refers to any living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Prevention" or "preventing" as used herein, includes, but is not limited to: (1) inhibiting the onset of a disease in a subject or patient which may be at risk and/or predisposed to the disease, wherein such inhibition may be either partial or complete, but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the terms "medication" or "therapeutic agent" refer to any compound and/or molecule that treats or prevents or alleviates the symptoms of disease or condition, including, but not limited to, a drug or pharmaceutical composition. Medication is considered to be delivered or present in therapeutically effective amounts or pharmaceutically effective amounts.

"Therapeutically effective amounts" or "pharmaceutically effective amounts", as used herein, means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, treatment may also merely reduce symptoms, improves (to some degree) and/or delays disease progression among other effects. It is not intended that treatment be limited to instances wherein a disease or affliction is cured. It is sufficient that symptoms are reduced.

As used herein, the terms "medical device," "implant," "device," "medical device," "medical implant," "implant/device," "drug delivery system" and the like are used synonymously to refer to any object that is designed to be placed partially or wholly within a patient's body for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. While medical devices are normally composed of biologically compatible synthetic materials (e.g., medical-grade stainless steel, nitinol, titanium and other metals; exogenous polymers, such as polyurethane, silicone, PLA, PLGA, PGA, PCL), other materials may also be used in the construction of the medical implant. While not limiting the present invention to any particular device, specific medical devices and implants that are particularly relevant to this invention include stents, punctal plugs, Crawford tubes, catheters, lacrimal tubes, ocular or other shunts, and drug delivery systems. In some embodiments, the device incorporates a contrast material or opaque materials that allow for visualization with standard imaging devices (for example, barium to allow for x-ray visualization).

As used herein, the term "medication reservoir" refers to any structure containing medication or therapeutic agent. In some embodiments, the reservoir is made of stretchy plastics or silicones. In some embodiments, the reservoir is substantially elastic. In some embodiments, the reservoir balloon may expand at least 500%. In some embodiments, the reservoir is substantially inelastic.

As used herein, the term "proximal" refers to a location situated toward a point of origin (e.g., between a physician and a lacrimal implant device or system).

As used herein, the term "distal" refers to a location situated away from a point of origin (e.g., behind a lacrimal implant device relative to a physician).

As used herein, the term "medicament" refers to any active agent that is suitable for use in medical treatment, such as a medicinal compound or drug.

As used herein, the term "active agent" refers to any molecular entity that exerts an effect on a living organism.

As used herein, the term "polymer" refers to any organic macromolecule containing one or more repeating units, as is well known in the art.

As used herein, a "copolymer" refers to any polymer in which there are at least two types of repeating units included. A copolymer can be a block copolymer, in which there are segments containing multiple repeating units of one type, bonded to segments containing multiple repeating units of a second type.

As used herein, the term "hydrophilic polymer" refers to any polymer that can be wetted by water, i.e., does not have a water-repellant surface. A hydrophilic polymer can absorb water to a small degree, for example about 0-100 wt percentage of water, but does not greatly swell in volume, as does a hydrogel-forming polymer.

As used herein, the terms "implanted" refers to having completely or partially placed a device or system within a host. A device or system is partially implanted when some of the device or system reaches, or extends to the outside of, a host.

As used herein, the term "steroids" refers to any organic compound that contains a core composed of twenty carbon atoms bonded together that take the form of four fused rings: three cyclohexane rings (designated as rings A, B, and C in the figure

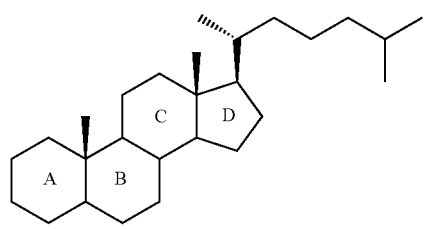

to the right) and one cyclopentane ring (the D ring). The steroids vary by the functional groups attached to this four-ring core and by the oxidation state of the rings. Examples of steroids include, but are not limited to, the dietary fat cholesterol, the sex hormones estradiol and testosterone, and the anti-inflammatory drug dexamethasone.

As used herein, the term "non-steroidal anti-inflammatory agents," "nonsteroidal anti-inflammatory drugs," usually abbreviated to NSAIDs or NAIDs, but also referred to as nonsteroidal anti-inflammatory agents/analgesics (NSAIAs) or nonsteroidal Anti-inflammatory medicines (NSAIMs), refers to any drug with analgesic and antipyretic (fever-reducing) effects and which have, in higher doses, anti-inflammatory effects.

As used herein, the term "antibiotics" refers to any compound or substance that kills or inhibits the growth of bacteria, fungus, or other microorganism.

As used herein, the term "anti-inflammatory agent" refers to any substance or treatment that reduces inflammation.

As used herein, the term "immunosuppressant agents" refers to all drugs that inhibit or prevent activity of the immune system.

As used herein, the term "anti-neoplastic agents" refers to all drugs that prevent or inhibit the development, maturation, or spread of neoplastic cells.

As used herein, the term "prostaglandin analogues" refers to all molecules that bind to a prostaglandin receptor.

As used herein, the term "nitric oxide" or "nitrogen monoxide" refers to any binary diatomic molecule with the chemical formula NO.

As used herein, the team "endothelin" refers to any protein that consisting of 21 amino acid residues that are produced in various cells and tissues, that play a role in regulating vasomotor activity, cell proliferation, and the production of hormones, and that have been implicated in the development of vascular disease. For example, endothelin biological activity may include, but is not limited to, constrict blood vessels, raise blood pressure, decrease eye pressure, and protect neuronal tissues from degeneration.

As used herein, the term "corticosteroids" refers to a class of chemicals that includes any naturally produced steroid hormone or synthetic steroid hormone analogue. Corticosteroids are involved in a wide range of physiologic processes, including, but not limited to, stress response, immune response, and regulation of inflammation, carbohydrate metabolism, protein catabolism, blood electrolyte levels, and behavior.

As used herein, the term "antibody-based immunosuppressants" refers to any antibody (e.g., polyclonal, monoclonal, Fab etc) having an immunosuppressant activity As used herein, the term "release of an agent" refers to any presence of the agent, or a subcomponent thereof, emanating from an implant device or system.

As used herein, the terms "analogue or analog" refer to any chemical compound that is structurally similar to a parent compound but differs slightly in composition (e.g., one atom or functional group is different, added, or removed). An analogue may or may not have different chemical or physical properties than the original compound and may or may not have improved biological and/or chemical activity. For example, the analogue may be more hydrophilic, or it may have altered reactivity as compared to the parent compound. The analogue may mimic the chemical and/or biological activity of the parent compound (i.e., it may have similar or identical activity), or, in some cases, may have increased or decreased activity. The analogue may be a naturally or non-naturally occurring (e.g., recombinant) variant of the original compound. An example of an analogue is a mutein (i.e., a protein analogue in which at least one amino acid is deleted, added, or substituted with another amino acid). Other types of analogues include isomers (enantiomers, diastereomers, and the like) and other types of chiral variants of a compound, as well as structural isomers. The analogue may be a branched or cyclic variant of a linear compound. For example, a linear compound may have an analogue that is branched or otherwise substituted to impart certain desirable properties (e.g., improve hydrophilicity or bioavailability).

As used herein, the term "derivative" refers to any chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." An analogue may have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). The term "derivative" also includes conjugates, and prodrugs of a parent compound (i.e., chemically modified derivatives that can be converted into the original compound under physiological conditions). For example, the prodrug may be an inactive form of an active agent. Under physiological conditions, the prodrug may be converted into the active fat n of the compound. Prodrugs may be formed, for example, by replacing one or two hydrogen atoms on nitrogen atoms by an acyl group (acyl prodrugs) or a carbamate group (carbamate prodrugs). More detailed information relating to prodrugs is found, for example, in Fleisher et al., Advanced Drug Delivery Reviews 19 (1996) 115 [1] incorporated herein by reference. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form, for example, alkali metal salts or alkaline earth metal salts (e.g., sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds that simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

As used herein, the term "inhibitor" or "antagonist" refers to any agent that prevents a biological process from occurring and/or slows the rate and/or slows the degree of occurrence of a biological process. The process may be a general one such as scarring or refer to a specific biological action such as, for example, a molecular process resulting in release of a cytokine.

As used herein, the term "agonist" refers to any agent that stimulates a biological process or rate or degree of occurrence of a biological process. The process may be a general one such as scarring or refer to a specific biological action such as, for example, a molecular process resulting in release of a cytokine.

As used herein, the term "anti-microtubule agent" should be understood to include any protein, peptide, chemical, or other molecule that impairs the function of microtubules, for example, through the prevention or stabilization of polymerization. Compounds that stabilize polymerization of microtubules are referred to herein as "microtubule stabilizing agents." A wide variety of methods may be utilized to determine the anti-microtubule activity of a particular compound, including for example, assays described by Smith et al. (Cancer Lett. 79(2):213-219, 1994) [2] and Mooberry et al., (Cancer Lett. 96(2):261-266, 1995) [3] both incorporated herein by reference.

Any concentration ranges, percentage range, or ratio range recited herein are to be understood to include concentrations, percentages or ratios of any integer within that range and fractions thereof, such as one tenth and one hundredth of an integer, unless otherwise indicated. In addition, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to both one polymer or a mixture comprising two or more polymers. As used herein, the term "about" means ±15%.

As used herein, the term "biomaterial" refers to any substance (other than drugs) or combination of substances synthetic or natural in origin, which can be used for any period of time, as a whole or as a part of a system which treats, augments, or replaces any tissue, organ, or function of the body.

As used herein, the term "biocompatibility" refers to the ability of a material to perform with an appropriate host response in a specific application.

As used herein, the term "elastic limit" or "yield strength" refers to the stress at which a material begins to deform plastically. Prior to the yield point the material will deform elastically and will return to its original shape when the applied stress is removed. Once the yield point is passed, some fraction of the deformation will be permanent and non-reversible.

As used herein, the term "elastic" refers to a material that with very large deformability when forces are applied on it with complete recoverability, meaning the object will return to its initial shape and size when these forces are removed. Such a feature has also been referred to as rubber elasticity. Molecular Requirements of such "elastic" materials: Material must consist of polymer chains, Need to change conformation and extension under stress. Polymer chains must be highly flexible. Need to access conformational changes (not w/glassy, crystalline, stiff mat.) Polymer chains must be joined in a network structure. Need to avoid irreversible chain slippage (permanent strain). One out of 100 monomers must connect two different chains. Connections (covalent bond, crystallite, glassy domain in block copolymer) Examples of elastic polymers include rubber, latex, synthetic rubbers, neoprene, silicone and the like.

As used herein, the term "non-elastic" or "nonelastic" refers to a material that with low or no deformability when forces are applied on it. Beyond the strain limit, a non-elastic material will experience irreversible deformation. Polymer chains are not flexible and do not easily access conformational changes. These may undergo irreversible chain slippage (permanent strain) Examples include glass, hard plastics, amorphous glassy polymers and the like.

As used herein, the term "semi-elastic" refers to a material that with moderate deformability when forces are applied on it with complete recoverability, meaning the object will return to its initial shape and size when these forces are removed. There are a number of semi-elastic polymers. Examples of semi-crystalline polymers are linear polyethylene (PE), polyethylene terephthalate (PET), polytetrafluoroethylene (PTFE) or isotactic polypropylene (PP).

As used herein, the term "stent" refers to any artificial 'tube' inserted into a natural passage/conduit in the body to prevent, or counteract, a disease-induced, localized flow constriction. The term may also refer to a tube used to temporarily hold such a natural conduit open to allow access for surgery.

As used herein, the term "shunt" refers to any artificial 'tube' inserted into the body to create a hole or passage to allow movement of fluids between two areas. Said tube may be implanted temporarily or may be permanent.

As used herein, the term "Foley catheter" refers to a flexible tube that is often passed through the urethra and into the bladder. The tube has two separated channels, or lumens, running down its length. One lumen is open at both ends, and allows urine to drain out into a collection bag. The other lumen has a valve on the outside end and connects to a balloon at the tip; the balloon is inflated with sterile water, or other fluid/gas, when it lies inside the bladder, in order to stop it from slipping out.

As used herein, the term "catheter" refers to any tube that can be inserted into a body cavity, duct, or vessel. Catheters thereby allow drainage, administration of fluids or gases, or access by surgical instruments. The process of inserting a catheter is catheterization. In most uses, a catheter is a thin, flexible tube ("soft" catheter), though in some uses, it is a larger, solid ("hard") catheter. A catheter left inside the body, either temporarily or permanently, may be referred to as an indwelling catheter. A permanently inserted catheter may be referred to as a permcath.

As used herein, the term "PLGA or poly(lactic-co-glycolic acid)" refers to a copolymer and is approved for therapeutic devices by the United States Food and Drug Administration (FDA), owing to its biodegradability and biocompatibility. PLGA has been studied for slow drug release [4].

As used herein, the term "polyethylene glycol" (abbreviated PEG) refers to any polyether compound. For example, PEG is commercially available as polyethylene oxide (PEO) or polyoxyethylene (POE), depending on its molecular weight (Carbowax®).

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 8A shows the inflated device/system by itself with an optional two tubes 10 for each punctum. FIG. 8B shows the major parts of the lacrimal system with which the device/system interacts. FIG. 8C shows an embodiment of the device/system in place with a filled reservoir balloon 2, wherein the tube 10 extends through the lower lacrimal duct to the lower punctum. FIG. 8D shows a device/system in place with a filled reservoir balloon 2 with a single set of tubes 10 terminating in a endcap 6, said endcap 6 in the upper (superior) punctum.

Figure 1:
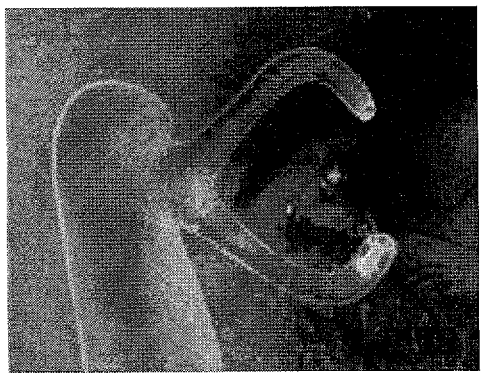
FIG. 1 shows an example of prior art punctal plugs that are inserted into the inferior punctum. Some punctal plugs are used a medication release platforms, but contain a very limited reservoir and depend upon natural interaction with the tear film and tear distribution for dispersal of the therapeutic agent.

LIST OF REFERENCE NUMERALS 1 the device/system
2 reservoir balloon
3 exit port
4 protective sleeve
5 flexible 'under-wire' or bracing structure
6 endcap
7 port
8 plug/flow limiting rod
9 plug peak
10 tube
11 lumen of the tube
12 secondary tube
13 egress track/tube
14 endcap opening of the egress track/tube
15 lacrimal sac opening of the egress egress track/tube
16 guide-wire
17 guide-wire central open lumen
18 secondary guide-wire
19 insertion catheter
20 medication/fluid composition with an active ingredient

DETAILED DESCRIPTION OF THE INVENTION

In order to eye treat infection, inflammation of the eye, glaucoma and other ocular diseases or disorders, drugs are often required to be administered to the eye. A conventional method of drug delivery is by topical drop application to the eye's surface. Topical eye drops, though effective, can be inefficient. As one example, when an eye drop is instilled in an eye, it often overfills the conjunctival sac (i.e., the pocket between the eye and the lids) causing a substantial portion of the drop to be lost due to overflow of the lid margin and spillage onto the cheek. In addition, a large portion of the drop remaining on the ocular surface can be washed away into and through a lacrimal canaliculus, thereby diluting the concentration of the drug before it can treat the eye. Moreover, topically applied drugs often have a peak ocular effect for about two hours post-application, after which additional applications of the drugs should be, but are often not, administered to maintain the desired drug therapeutic benefit.

To compound ocular management difficulty, patients often do not use their eye drops as prescribed. This poor compliance can be due to, for example, an initial stinging or burning sensation caused by the eye drop and experience by a patient. Instilling eye drops in one's own eye can be difficult, in part because of the normal reflex to protect the eye. Therefore, one or more drops may miss the eye. Older patients may have additional problems instilling drops due to arthritis, unsteadiness, and decreased vision. Pediatric and psychiatric populations pose difficulties as well.

Conditions of dry eye have been treated by blocking the tear flow from the eye into and through the lacrimal canaliculus. This has involved closing the canalicular canal by stitching the punctal opening shut or by using electrical or laser cauterization to seal the punctal opening. Although such procedures can provide the desired result of blocking tear flow to treat a dry eye, they are unfortunately not reversible without reconstructive surgery.

In a field different from ocular management, control of respiration-related (e.g., allergies) diseases or disorders often requires repetitive manual digestion or other intake of a medication, and as such, can be ineffective due to a lack of patient compliance or non-localized drug delivery.

Therapeutic Devices

There have a variety of therapeutic devices designed to address eye and lacrimal system related conditions. Primary amongst them are lacrimal punctal plugs. There are several devices, which have useful features, yet do not have the advantages of the current invention.

In one reference, Sim, S. et al. "Composite Lacrimal Insert and Related Methods," United States Patent Application 20100034870 application Ser. No. 12/432,553, filed Apr. 29, 2009 [5], discloses a removable, drug-releasing lacrimal implant owned by QLT. The plug is implanted into a lacrimal punctum of a subject. Such a punctal plug comprise to a drug core that erodes with delivery to the tear film, dependent on tear movement to dissolution of the drug core. The drug core is sedentary and the tears are required to flow in and out of the reservoir for drug distribution. The reference does not describe an extended plug connected to a reservoir located in the lacrimal sac of the current invention.

In another reference, Hubbell, J. A. et al. "Photopolymerizable Biodegradable Hydrogels as Tissue Contacting Materials and Controlled-Release Carriers," U.S. Pat. No. 5,410,016 filed Mar. 1, 1993 [6], discloses a biodegradable PEG based system also used for punctal plug delivery owned by Ocular Therapeutix. The reference does not describe an extended plug connected to a reservoir located in the lacrimal sac of the current invention.

In another reference, Rodstrom, T. R. et al. "Punctal Plugs and Methods of Delivering Therapeutic Agents," United States Patent Application 20080181930 filed Jan. 30, 2008 [7], discloses another punctal plug drug delivery system with a matrix of a silicone and an ophthalmic drug with a parylene polymer coating on a portion of the outer surface. The method of drug delivery is passive utilizing the dissolution of the drug into the tear film of the eye. The plug and an extended portion, but lacks the reservoir of the current invention.

In another reference, Borgia, M. J. et al. "Punctal Plugs for the Delivery of Active Agents," United States Patent Application 20070298075 filed Jun. 7, 2007 [8], discloses another example of punctal plugs with slow release drug delivery. The reference does not describe reservoir of the current invention.

In another reference, Brubaker, M. J. et al. "Sustained Release Drug Delivery Devices," WIPO Patent Application WO/2002/056863 Application PCT/US2001/048804, filed Jul. 25, 2002 [9], discloses another plug device for distribution of a medication. The reference does not describe an extended plug connected to a reservoir located in the lacrimal sac of the current invention.

In another reference, Rapacki, A. R. et al. "Lacrimal Implants and Related Methods," United States Patent Application US 2010-0274204 A1 filed Feb. 23, 2010 [10], discloses another lacrimal drug delivery device which is an extended version of a punctal plug, with an additional anchoring arm that extends down the lacrimal duct when inserted. The reference describes the use of "balloons" as structural elements to position the device, not as drug containing reservoirs. The reference does not describe a reservoir located in the lacrimal sac of the current invention.

In another reference, Cohan, B. E. "Opthalmic Insert and Method for Sustained Release of Medication to the Eye," European Patent EP1891942B1 Application EP1178779A1, filed Apr. 7, 2000 [11], discloses an apparatus for intubation of lacrimal duct (lacrimal drainage pathway) for treatment of lacrimal duct obstruction. Additionally, the internal portion of the device may act as a reservoir of medication that may be released through a pore on the device in a controlled manner based upon a specific geometry of the device. This controlled rate is still based upon tear dissolution of the medication and penetration of the reservoir by the tear film. The reference does not describe a balloon reservoir or a reservoir located in the lacrimal sac of the current invention.

In another reference, Murube, J. et al. (2003) Subcutaneous Abdominal Artificial Tears Pump-Reservoir for Severe Dry Eyes, *Orbit* 22(1), 29 [12], discloses a study of an implanted pump-reservoir unit placed under the subcutaneous tissue of the abdomen for providing artificial tears to the ocular surface in patients with severe dry eye. While this system does provide for a reservoir, the system uses an electrical pump and the reservoir's location is far from the lacrimal sac. The reference does not describe a balloon reservoir or a reservoir located in the lacrimal sac of the current invention.

Another reference, U.S. patent application Ser. No. 11/641,903 by Freilich [13] has many limitations that make it unusable including, but not limited to:

1. The faceplate is the site of control for resistance of outflow. This would not work in practical terms. In order to be flow limiting, one would need a larger (longer) barrier to flow as in the current device as noted above. The prior art is very vague regarding what is driving the flow. In a system where there is active pressure pushing the fluid out, the resistance is dependent on the pressure drop in the system. The lower the pressure drop then the lower the resistance needed etc. Practically speaking both long "low" resistance plugs and short "high" resistance plugs could work. Both approaches have benefits. Firstly, the long low resistances plug may not be dependent on the driving pressure of the balloon. This could be good if the rate of flow through the plug has another driver out of the balloon (capillary etc). Second, a short high resistance plug is potentially driven with simple pressure drop over a resistance. Length of resistance is an important factor in flow resistance but equally important is the pressure drop (if pressure driven flow) and the diffusion rate (pressure independent flow). Freilich [13] does not differentiate between these two types of pressure. The current invention contemplates both a long lower resistance plug and a small high resistance plug as alternatives, or in one embodiment in combination.

2. The Freilich device includes an expandable reservoir connected to a tube and then connected to the flow limiting plate. The tube as described in the Freilich application will not allow for reliable implantation and reliable flow. This is a critical difference from the current invention. The current invention device comprises more than simply a tube connecting the reservoir to the faceplate. In one embodiment, the present invention device will require the plug (in one embodiment silicone hydrogel) to extend from the reservoir all the way (or most of the way) to the endcap, which may be a faceplate. Therefore, the current invention will not simply have a tube connecting the reservoir to the endcap . . . it will be a flow limiting plug or rod. This will also allow the hydrogel to act as a wick from the balloon to the tear surface and will also prevent any kinking post implantation. It should also be noted that the Freilich application [13] states "As a result of the structure of device 300, there is provided an open channel or passageway that extends from the opening 202 of collarette 200, through the entire length of the stent 310" This is the focus of the Freilich device. The current invention bypasses this limitation as noted above.

3. Freilich teaches a collertte that resides against the punctum and the eye. The current invention device will have a hydrogel plug that resides substantially behind the border of the endcap (domes out) so that it is in contact directly with the ocular surface and allows exchange of drug directly to the tear film. As such, the mechanism of delivery of the current invention consists of both a movement of the drug from the balloon to the endcap, but also an osmolar drive of drug from the hydrogel to the tears. There is significant discussion in Freilich [13] about holes and openings that allow for medication communication with the eye while using holes will not work consistently. The current invention bypasses that with the above description.

4. The Freilich patent discusses and expandable reservoir [13]. It does not teach a balloon like mechanism like (U.S. Pat. No. 6,196,993 to Cohan et al [14]). The current invention teaches a balloon like reservoir that acts as a low-pressure force (Freilich discloses a pump like mechanism "expandable pouch is filled with medication and the medication is thereafter permitted to flow naturally (e.g., through capillary action), through digital pressure applied by the patient to the nasal lacrimal sac, and or with assistance of a miniature pump." Further, the Freilich patent does not describe pressure driven flow from the balloon, but specifies a "pumping mechanism." The current invention balloon reservoir is elastic so that the driving force of fluid is minimal.

5. The method that Freilich [13] employs filling the device does not appear to have practical application as using a syringe with soft tip to reach in and then go half way out before filling will lead to bubbles forming in the balloon. The current invention contemplates a method of filling from the bottom up is key. Bubbles can be excluded. Having bubbles in this system will cause poor reliability and even failure of flow.

DETAILED DESCRIPTION OF AN EXEMPLARY EMBODIMENT

The current invention involves an implanted medical device designed as a lacrimal system for drug delivery.

In one embodiment, the invention comprises a "plunger" type device with a silicone hydrogel plug 8. The device 1 may include a reservoir balloon 2 coupled to a tube 10 that extends through the lacrimal duct to the punctum. The tube 10 may include an endcap 6 or faceplate that abuts against the punctum and prevents the tube 10 from retracting into the lacrimal duct. A guide-wire 16 may be provided for insertion of the device 1. In one embodiment, the device 1 is advanced into the lacrimal system using an insertion catheter 19. Once the device 1 is inserted, the reservoir balloon 2 may be filled with a fluid 20 and retraction of a silicone hydrogel 8 or similar material from the device 1 to plug up the lumen 11 of the tube 10 that leads to an endcap 6 and thus control egress of fluid 20 to the tear film. In one embodiment, the device 1 enables a method for filling the reservoir balloon 2 from the bottom up and then leaving the plug 8 behind. The plug 8 may reside significantly within the tube 10 of the device rather than entirely within the endcap 6. The length of the plug 8 may be used to control delivery since anything at just the endcap 6 would be open to trauma and will leave little room for complexity. In one embodiment, the plug 8 spans the distance from just beyond the endcap 6 to the reservoir balloon 2. In one embodiment, the plug 8 may occupy anywhere between $\frac{1}{32}$ to the full distance between the endcap 6 and the reservoir balloon 2. In one embodiment, the tube 10 comprises medical grade silicone. In one embodiment, the device 1 does not have a tube 10, but rather only comprises a plug 8 spanning the distance between the endcap 6 to the reservoir balloon 2.

In one embodiment, the length of the plug 8 may vary. In one embodiment, the plug 8 length may vary from an endcap 6, such as a faceplate, all the way to the reservoir balloon 2 and anywhere in between. In some embodiments, the plug 8 is generally flush with the endcap 6. In some embodiments, the plug 8 extends distally past the endcap 6 from approximately 1-200 microns to comprise a plug peak 9. The endcap 6 may be integrally connected to the tube 10. In other embodiments, the endcap 6 is coupled to the tube 10 by an adhesive or one or more fasteners. In some embodiments, the endcap 6 may have a diameter of 1-2.5 mm. It may be oval with the long dimension at 2 mm and the short dimension at 1 mm. It may be circular or oval or square. The height of the endcap 6 may range from 20 microns to 300 microns. In some embodiments, the endcap 6 may taper at the end from 300 μm at the apex to 10 microns at the edges. The flow-limiting plug 8 may protrude past the apex of the endcap 6 by 1 μm to 50 μm to comprise a plug peak 9. In some embodiments, the protruding portion of the plug may be displaced from the apex of the endcap 6 towards one of the edges of the endcap 6 to enhance contact with the tear film. In one embodiment, the plug 8 is a silicone hydrogel plug. In one embodiment, the plug 8 is a non-silicone hydrogel plug. In one embodiment, the plug material may be selected from the group comprising nano-spheres, microspheres, filter membranes, porous membranes, porous materials such as foams and solid materials such as polymers with textured outer surfaces that will allow fluid to flow around etc. In one embodiment, the plug 8 comprises materials with grooves. In one embodiment, said grooves are flow limiting tortuous paths for flow. In one embodiment, plug 8 provides an occluding mechanism. In one embodiment, the plug 8 may be colorless or may be blue, red, or yellow. In one embodiment, the plug 8 contains fluorophores to provide for a distinction from surrounding materials and tissues. In one embodiment, the silicone hydrogel plug 8 may also contain materials that allow it to fluoresce after exposure to a specific wavelength of light. In one embodiment, the plug 8 spans the distance from just beyond the endcap 6 to the reservoir balloon 2. In one embodiment, the plug 8 may occupy anywhere between $\frac{1}{32}$ to the full distance between the endcap 6 and the reservoir balloon 2. In one embodiment, the tube 10 comprises medical grade silicone. In one embodiment, the device 1 does not have a tube 10, but rather only comprises a plug 8 spanning the distance between the endcap 6 to the reservoir balloon 2. In one embodiment, the plug 8 comprises a flow limiting rod.

Device Implantation

To be effectively placed in the lacrimal system and properly deliver therapeutic agents to the tear film of the eye, the device may be deliverable by tracking through the tortuous and narrow anatomy. To do this, the dimensions have to be very small and in an uninflated state (e.g., <1 mm in diameter). In one embodiment, the invention further comprises a delivery system that includes a guide-wire 16 combined with an inflation device. In one embodiment, the invention further comprises an insertion catheter 19. In one embodiment, said guide-wire 16 comprises a central open lumen 17. In one embodiment, said central open lumen 17 is flexible. In one embodiment, said central open lumen 17 allows injection of fluid distal directly into the balloon reservoir 2. In another embodiment, the delivery system is enhanced by internal characteristics of the device. In one embodiment, the device comprises a secondary guide-wire 18 that extends the external length of said device. In one embodiment, the device further comprises a stiff but flexible 'under-wire' that gives the reservoir balloon 2 bracing structure 5. In one embodiment, no secondary guide-wire 18 is needed to travel the length since there is a stiff but flexible 'under-wire' that gives the device some push-ability. In this embodiment, the inflation device connects proximal to the endcap.

Figure 10:
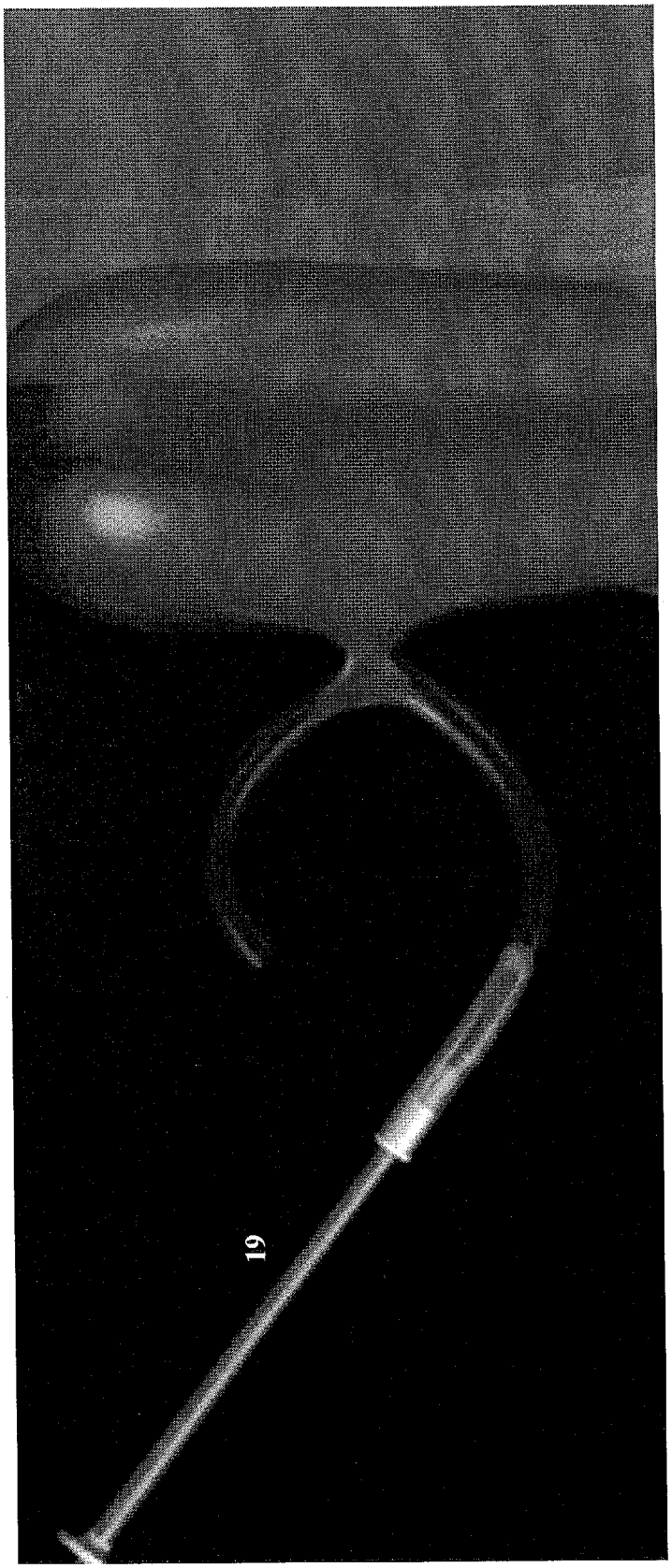
FIG. 10 shows the device advanced into the punctum.
Figure 11:
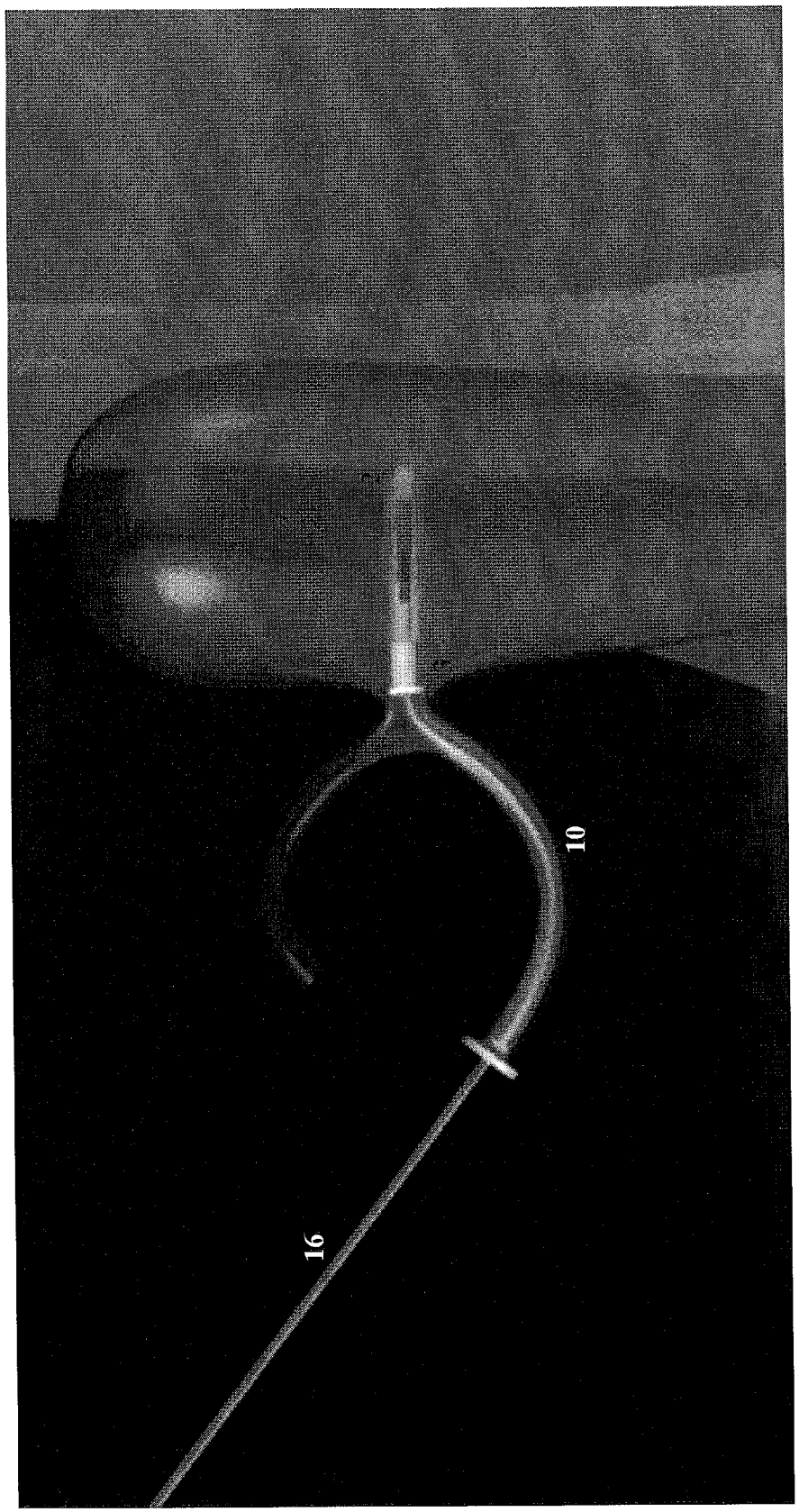
FIG. 11 shows the device advanced into the lacrimal sac through the lower lacrimal duct.
Figure 12:
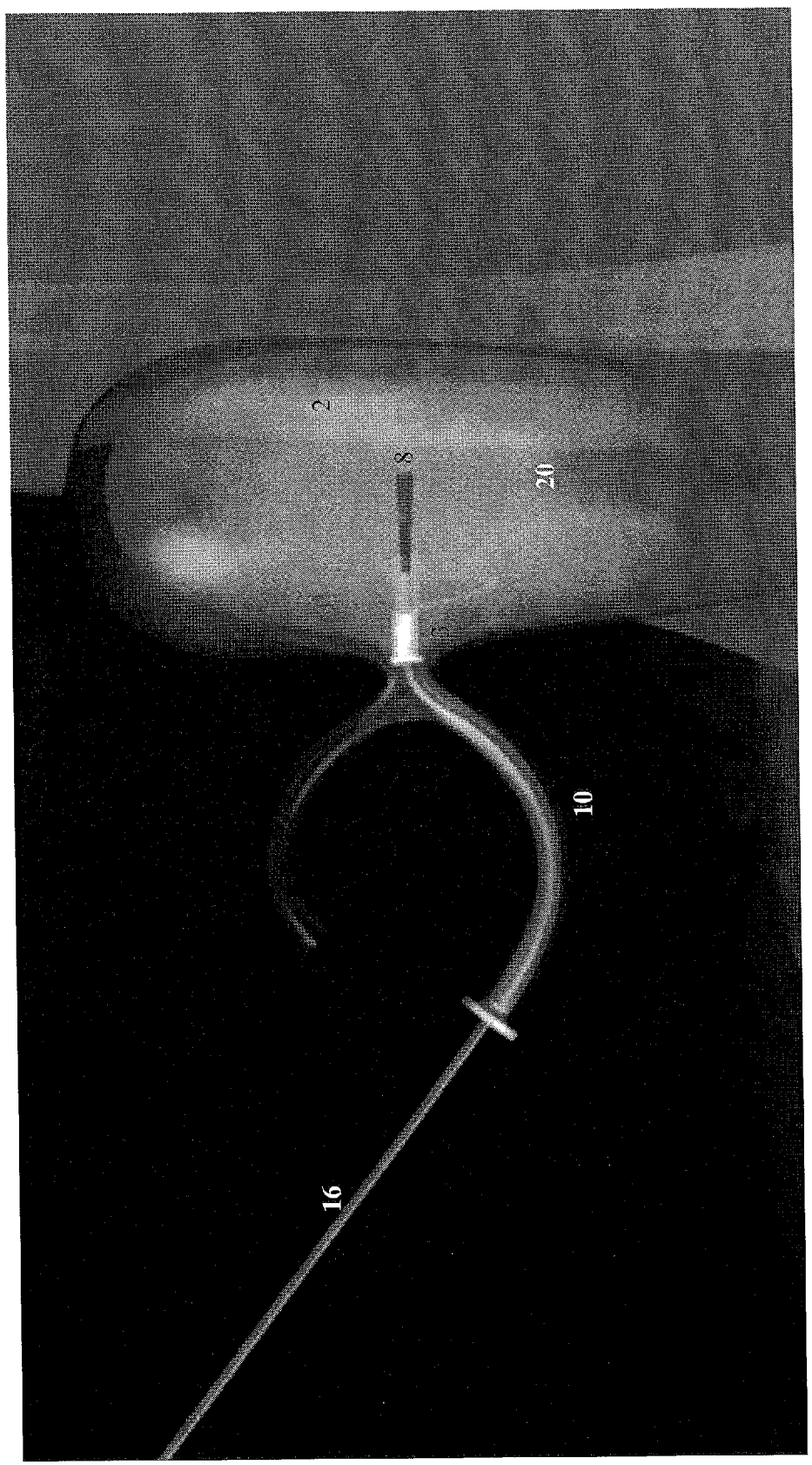
FIG. 12 shows the device reservoir inflated in the lacrimal sac.
Figure 13:
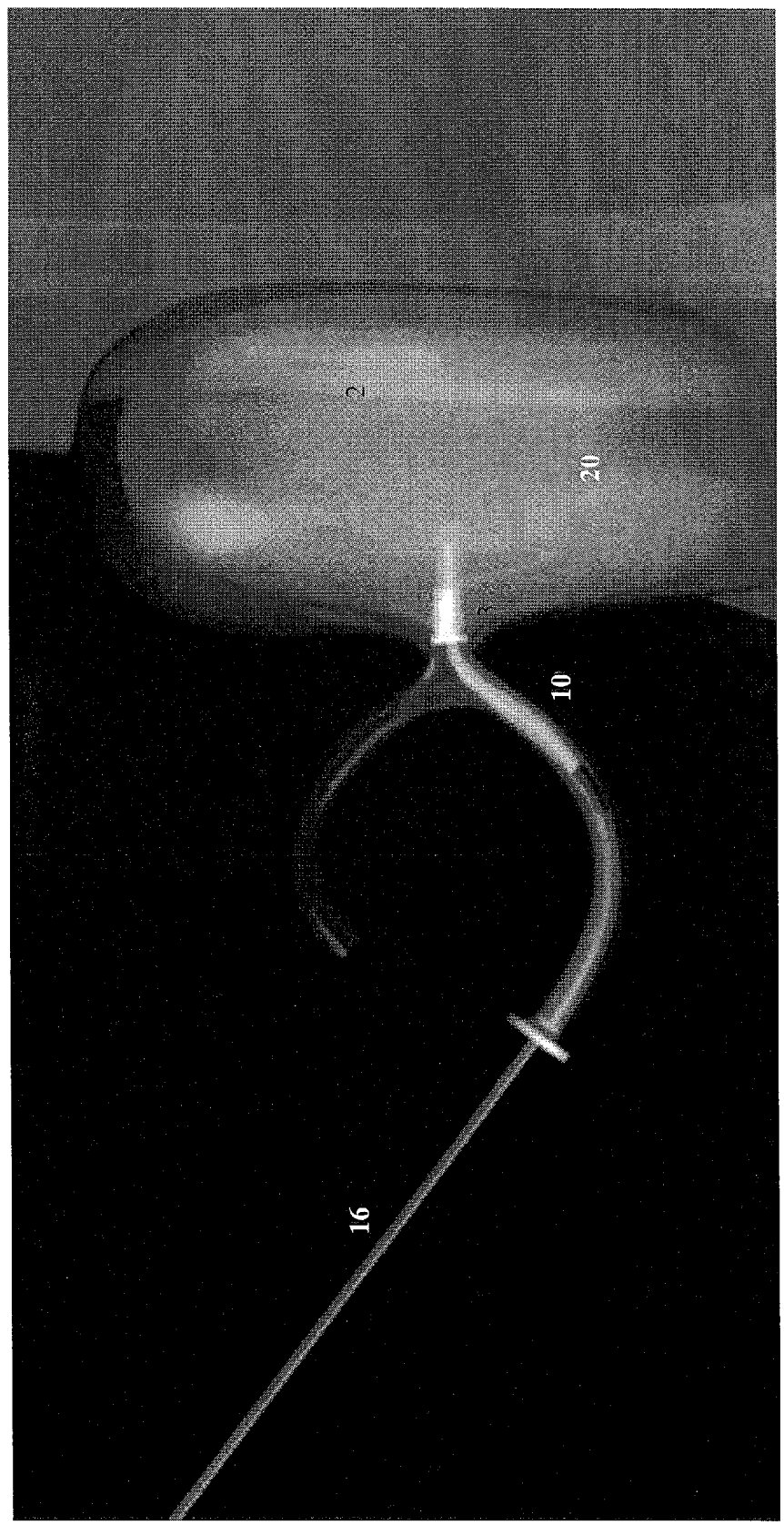
FIG. 13 shows the flow-limiting plug retracted from the distal end of the device.
Figure 14:
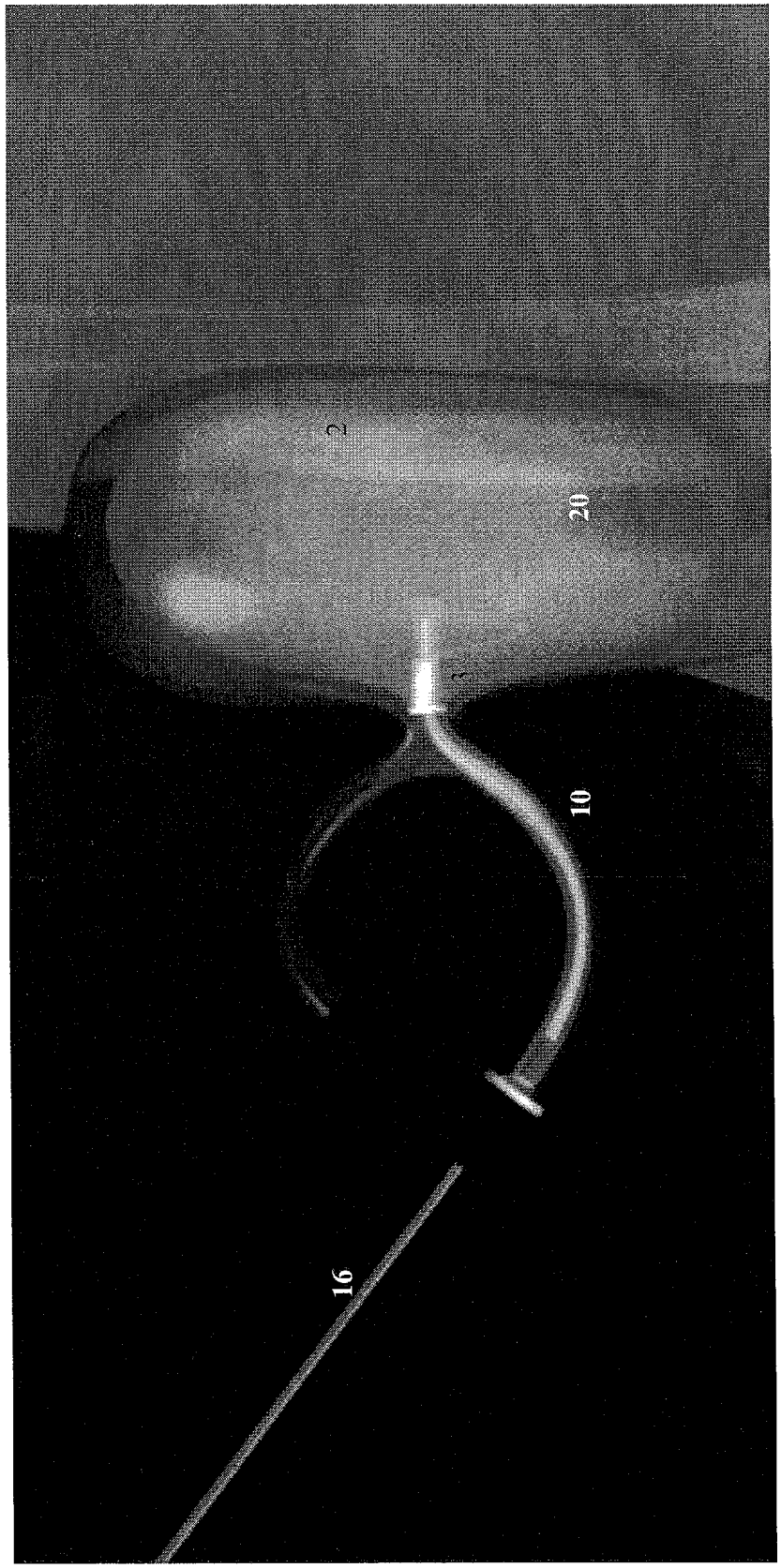
FIG. 14 shows the insertion catheter fully retracted leaving flow-limiting plug in place.
Figure 15:
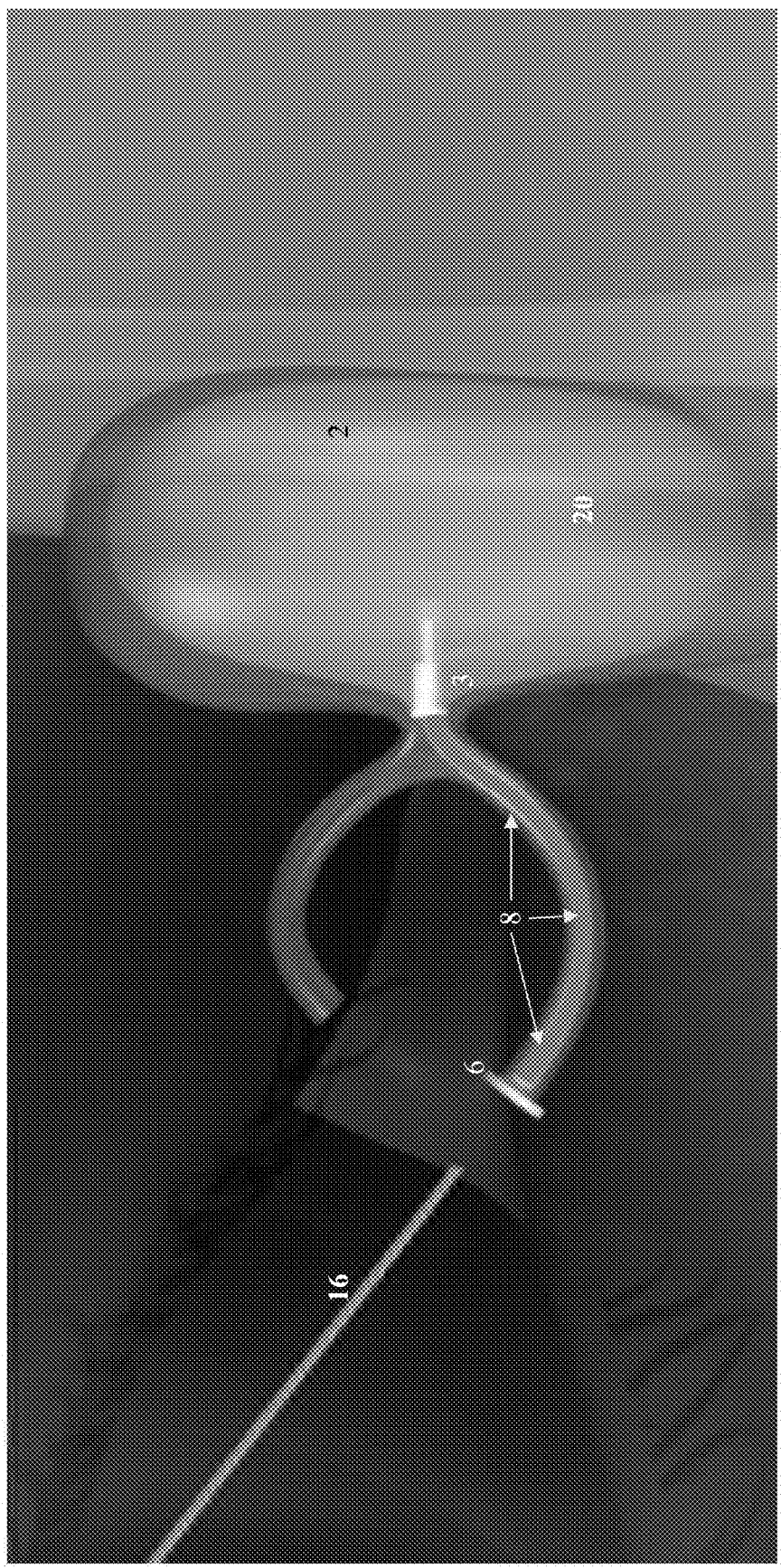
FIG. 15 shows the insertion catheter fully retracted leaving flow-limiting plug 8 in place, wherein the plug 8 occupies the entire length between the endcap 6 and the reservoir balloon 2.

The device may be inserted using an insertion catheter as shown in FIG. 10-FIG. 15. FIG. 10 shows the device 1 advanced into the punctum. FIG. 11 shows the device 1 advanced into the lacrimal sac through the lower lacrimal duct. FIG. 12 shows the device 1 reservoir balloon 2 inflated in the lacrimal sac. The device 1 reservoir balloon 2 is inflated through the lumen of either the guide-wire 16 or the device lumen 11. FIG. 13 shows the flow-limiting plug 8 retracted from the distal end of the device 1. FIG. 14 shows the insertion catheter 19 and guide-wire 16 fully retracted leaving the flow-limiting plug 8 in place. FIG. 15 shows a version of the device wherein the insertion catheter 19 and guide-wire 16 fully retracted leaving the flow-limiting plug 8 in place, wherein the plug 8 occupies the entire length between the endcap 6 and the reservoir balloon 2.

Figure 9:
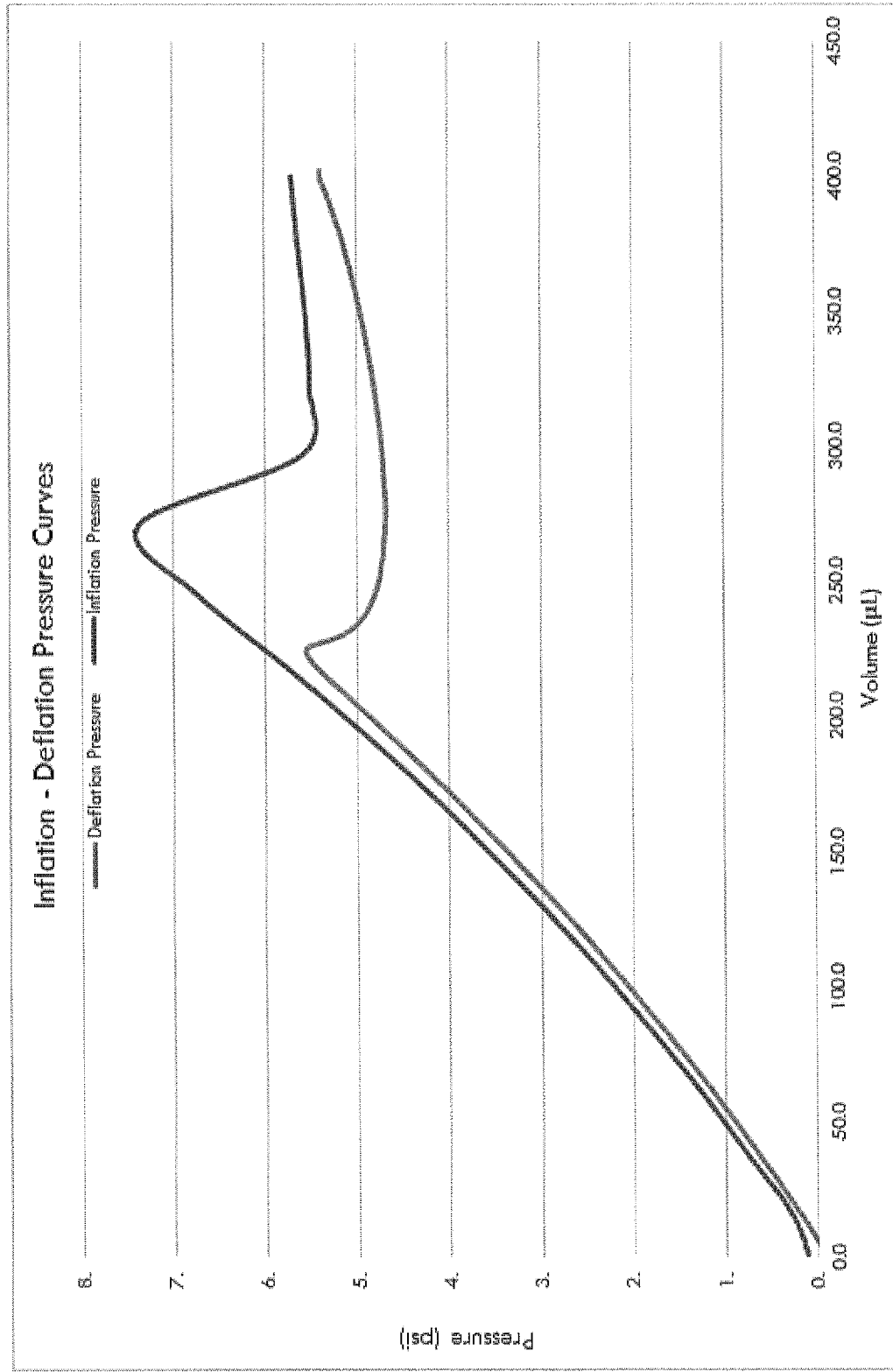
FIG. 9 shows an example of a reservoir balloon 2 inflation/inflation curve for one embodiment of the current invention.

The lacrimal drug delivery system of the current invention may be inflatable while in situ and be able to contain the proper amount of drug. To do this and maintain the initial low profile size the balloon reservoir may expand from its uninflated state to fill with enough drug to provide the continual delivery that is contained. In one embodiment, expansion of said balloon reservoir is at least 500%. In one embodiment, such the volume of said inflated balloon reservoir is at least 100 micro liters. In one embodiment, said balloon reservoir comprises silicone. Silicone is especially good for this application since it has high elongation inflation with very low pressures. Initial testing showed peak inflation pressures less that 6 psi (see e.g., FIG. 9). It is an important consideration, when compared to the slow flow rates that is needed, providing balloon pressure comprises the driving force. The lower the driving pressure, the easier it may be to create the resistance provided by the plug needed to reach that flow rate.

In one embodiment, the invention relates to a method of treatment, comprising: a) providing: i) a subject comprising a punctum, lacrimal ducts, and a lacrimal sac, ii) a lacrimal system drug delivery device, comprising: A) a reservoir balloon having an exit port, wherein said reservoir balloon is capable of insertion inside said lacrimal sac, B) a tube comprising at least one lumen fluidly coupled to said exit port, wherein said tube extends from said elastic reservoir through at least one of the lacrimal ducts, C) an endcap comprising a port fluidly coupled to the terminal end of said tube wherein said endcap interfaces with said punctum in contact with the tear film of the eye, and D) a plug, wherein the plug resides within the lumen of said tube of the device, and b) inserting said drug delivery device into said lacrimal system; c) filling said reservoir balloon with composition with at least one active ingredient; and d) administering said composition to said subject using said lacrimal system drug delivery device. In one embodiment, said device further comprises a guide-wire attached to said plug. In one embodiment, said composition with at least one active ingredient further comprises a therapeutic agent. In one embodiment, filling comprises introduction of said composition with at least one active ingredient through said tube. In one embodiment, step c) further comprises removal of said guide-wire attached to said plug, wherein said plug obtains a final position within the lumen of said device up until the endcap of said device. In one embodiment, said device further comprises at least one egress track connecting said endcap to outside of said reservoir balloon. In one embodiment, said egress track is designed to allow tears to flow from the ocular surface into the lacrimal sac and beyond. In one embodiment, said plug regulates the flow of said composition from said device. In one embodiment, said plug positioning within said lumen regulates the flow of said composition from said device. In one embodiment, the plug spans the distance from just beyond the endcap to the reservoir balloon. In one embodiment, the plug may occupy anywhere between 1/32 to the full distance between the endcap and the reservoir balloon. In one embodiment, the tube comprises medical grade silicone. In one embodiment, the device does not have a tube, but rather only comprises a plug spanning the distance between the endcap to the reservoir balloon. In one embodiment, the plug comprises a flow-limiting rod. In one embodiment, said guide-wire comprises a central open lumen. In one embodiment, said guide-wire is occupies a lumen of said device for delivery of said device into position. In one embodiment, said central open lumen is flexible. In one embodiment, said central open lumen allows injection of fluid distal directly into the balloon reservoir. In another embodiment, the delivery system is enhanced by internal characteristics of the device. In one embodiment, the device comprises a secondary guide-wire 18 extends the external length of said device. In one embodiment, the device further comprises a stiff but flexible 'under-wire' that gives the reservoir balloon bracing structure. In one embodiment, the inflation device connects proximal to the endcap. In one embodiment, the reservoir balloon is substantially elastic. In one embodiment, the reservoir balloon is semi-elastic. In one embodiment, the reservoir balloon is substantially nonelastic. In some embodiments, the device comprises a protective sleeve be placed over said reservoir balloon. In one embodiment, said sleeve protects against leaks entering the nasal duct or other tissue compartments. In one embodiment, said device contains fluorescent material or coloring to allow for detection and position confirmation by the user (physician or patient). In one embodiment, the method further comprises filling said reservoir balloon with a therapeutic agent or medication. In one embodiment, said reservoir balloon is implanted within the sinuses surrounding the eye. In one embodiment, the punctal portion or endcap allows for filling the reservoir balloon with medication, but the reservoir balloon sits in a sinus and allows for delivery of drug through the plug to the tear film of the eye. In one embodiment, expansion of said balloon reservoir is at least 500%. In one embodiment, expansion of said balloon reservoir is at least 700%. In one embodiment, such the volume of said inflated balloon reservoir is at least 100 micro liters. There are not many types of balloons that could do this. In one embodiment, said balloon reservoir comprises silicone. In one embodiment, said reservoir balloon enables anatomical fixation. In one embodiment, fixation is achieved by the balloon inflating beyond the diameter of the proximal common canaliculus thus preventing it from extruding back into the proximal lacrimal outflow system. In one embodiment, said anatomical fixation is a device retention feature. In one embodiment, said plug regulates the flow of said composition from said device. In one embodiment, said plug positioning within said lumen regulates the flow of said composition from said device. In one embodiment, said active ingredient consists of artificial tears, glaucoma drops, anti-inflammatory agents, nonsteroidal agents, antibiotics, biologics, proteins, aptamers, nucleic acids, cytokines, plasma, sympahtomemetics, parasympathomemetics, prostaglandin analogues, beta blockers, alpha-agonists, and anti-VEGF agents. In one embodiment, the flow of said fluid out of said device is controlled by adjustment of said plug by an operator (patient or physician) to decrease flow at given times of the day when treatment might not be needed (while sleeping for example). In one embodiment, the reservoir balloon will deliver fluid+/−active ingredients to the ocular surface at a fixed rate between 0.1 micro liters and 30.0 micro liters per day for a minimum of one week. In another embodiment, the delivery is achieved for a minimum of 60 days.

In one embodiment, the tube has multiple lumens such that the hydrogel, guide-wire or inflation lumens are all each separate lumens. In the preferred embodiment, all three (the hydrogel plug, the guide wire, and the reservoir balloon inflation lumen) utilize the same lumen. In one embodiment, the hydrogel/plug material is delivered through the inflation lumen. In one embodiment, the plug is tethered to the bottom (distal part) of the reservoir balloon so that expansion of the balloon is limited in the long access and drives expansion of the balloon to the sides instead.

Once the device is delivered and filled, the balloon reservoir delivers the fluid containing the therapeutic agent at a slow rate. There are several viable ways to affect therapeutic agent delivery. First, for pressure driven flow, the lower the pressure drop the lower the resistance needs to be to create the right flow rate. A second method, ignores the pressure completely. The methods to drive flow in these cases includes a wicking or transport phenomena that occurs in fluid filled hydrogels or some types of membrane filters. The benefits to these approaches are that the pressure in the balloon is no longer a variable in the flow rate, which leads to constant drug delivery if the pressure changes during deflation. In one embodiment, the plug provides a fluid hydrogel to facilitate the delivery of the therapeutic agent from the reservoir balloon through the lumen to the endcap of the device and beyond to the tear film of the eye.

Figure 2:
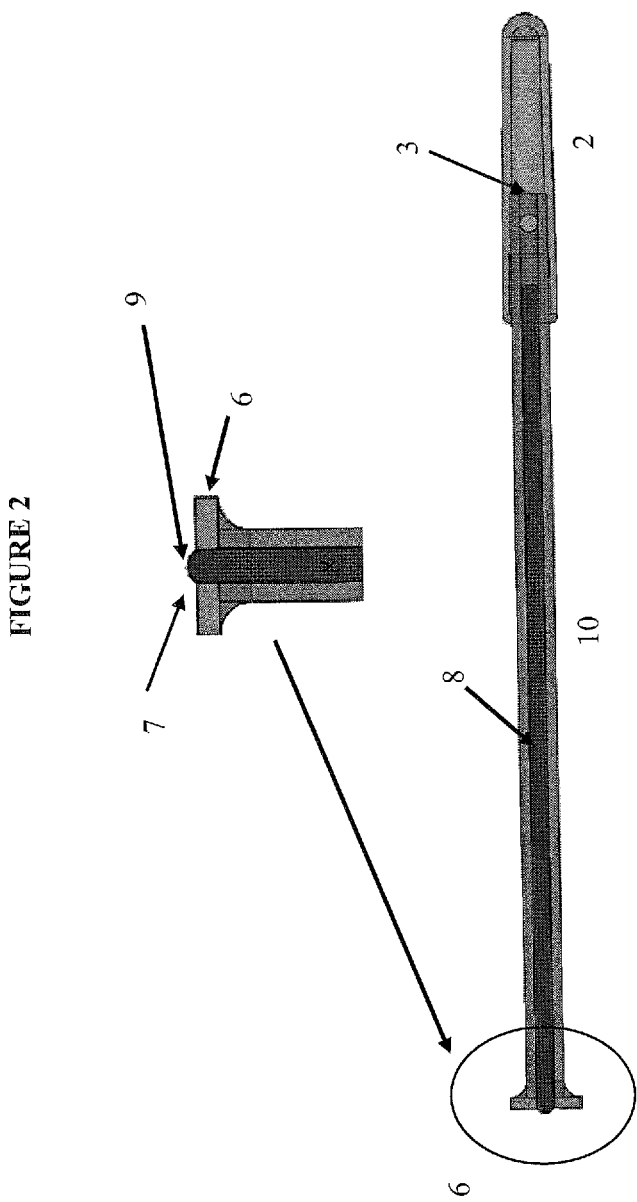
FIG. 2 shows an example of the current invention's design. The plug peaks 9 from the surface of the endcap 6 for 1-200 microns. This allows direct contact between the plug 8 and the tear film of the eye. The lumen 11 of the tube 10 is occupied by a silicone hydrogel plug 8. The plug 8 occludes the lumen 11 for a substantial length and may act as a wicking device to assist in travel of the medication from the reservoir balloon 2 to the tear film of the eye. The plug 8 also controls rate of flow.
Figure 3:
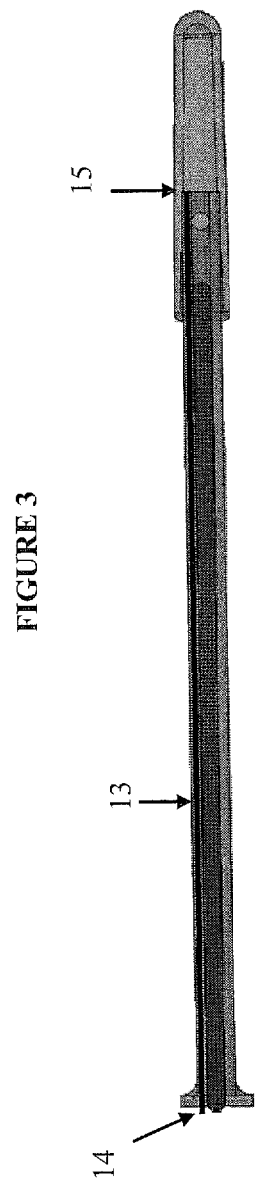
FIG. 3 shows one example of the current invention's design with the egress track 13.
Figure 4:
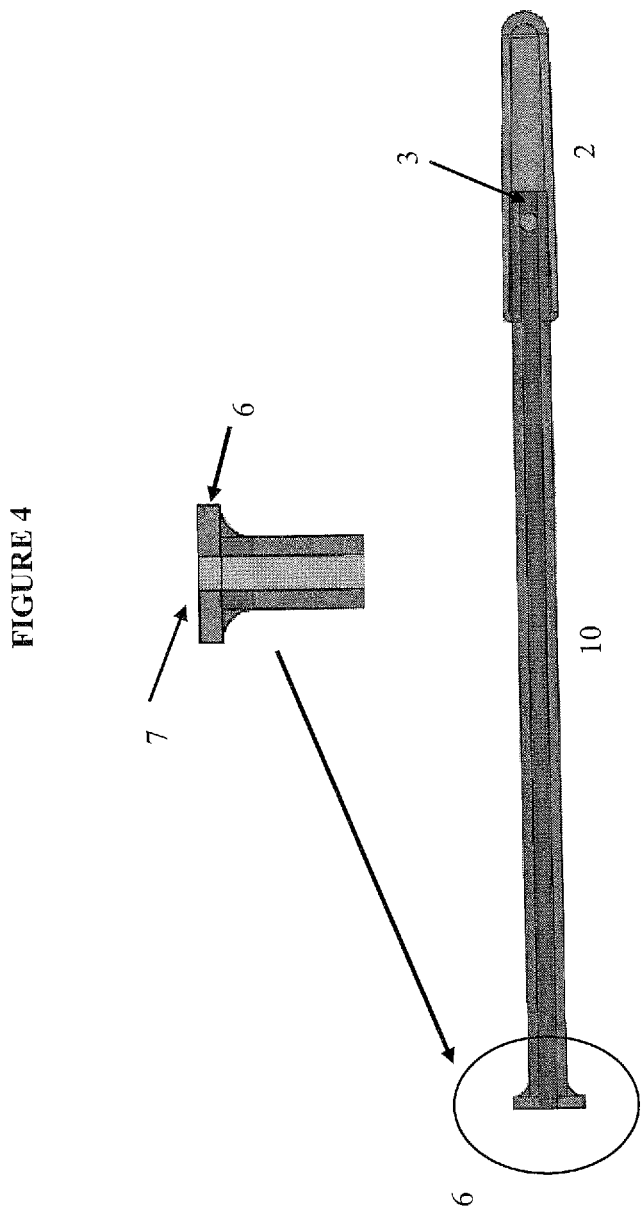
FIG. 4 shows an example of the current invention's design without the plug. The lumen 11 of the tube 10 is connected to the endcap 6 through the port 7 and connects to the reservoir balloon 2 through the exit port 3.
Figure 5:
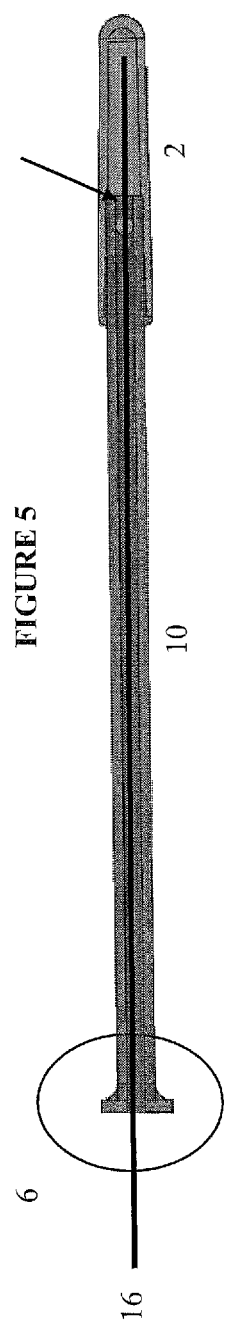
FIG. 5 shows an example of the current invention's design without the plug in the lumen 11 of the tube 10, but rather having the guide-wire 16 threading through the device/system to guide the device/system during the insertion process and before the reservoir balloon 2 is inflated with medication 20 and the plug 8 is installed. The lumen 11 of the tube 10 is connected to the endcap 6 through the port 7 and connects to the reservoir balloon 2 through the exit port 3.
Figure 6:
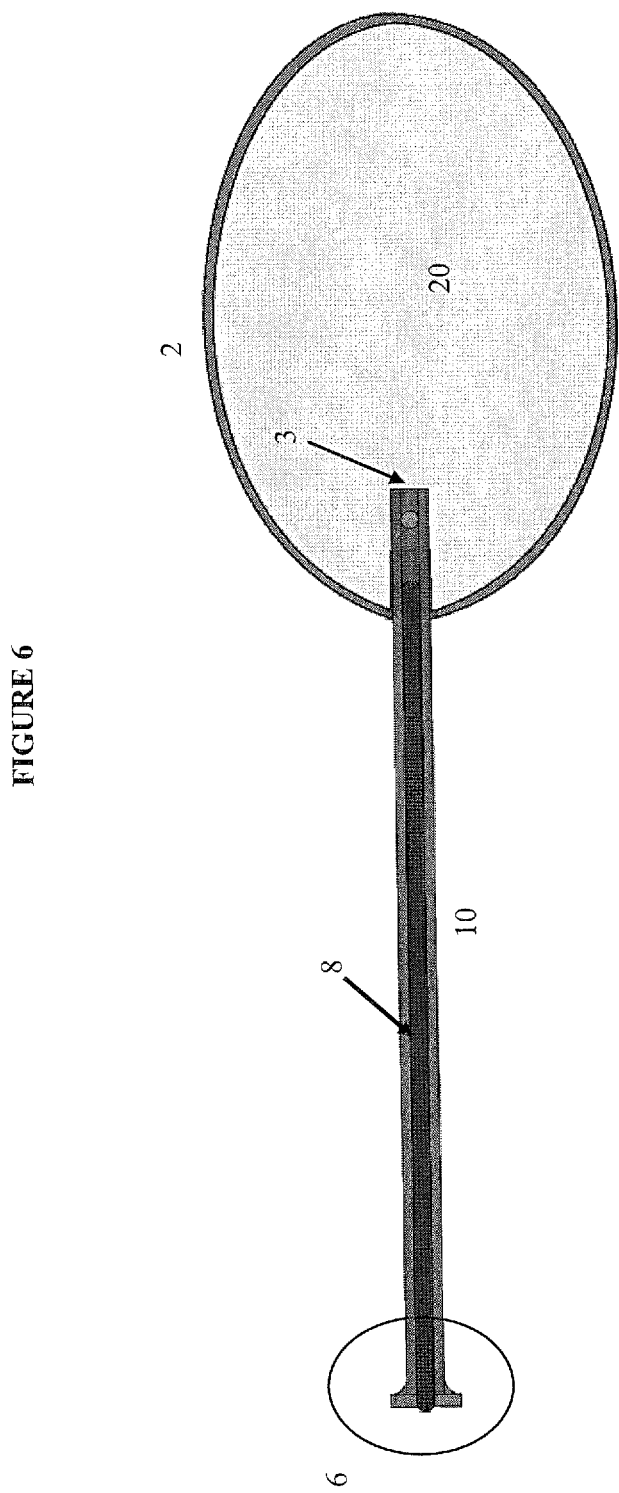
FIG. 6 shows an example of the current invention's design wherein the reservoir balloon 2 is inflated with medication 20 and the plug 8 is installed.
Figure 7:
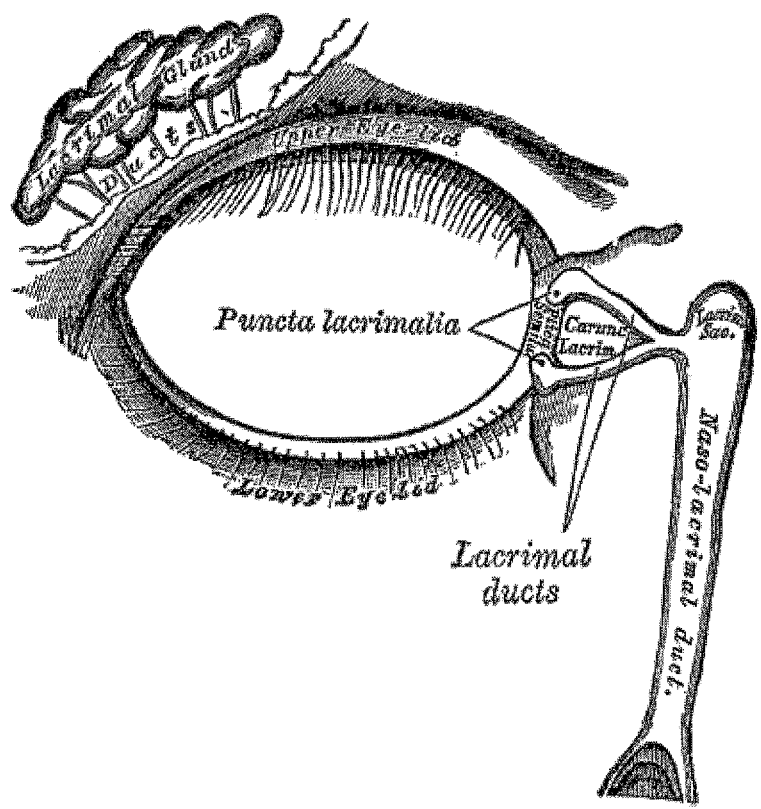
FIG. 7 shows a diagram of the lacrimal system. Herein, the upper and lower lacrimal ducts converge into the nasolacrimal duct. The device/system is envisioned to extend from the reservoir located in the lacrimal sac and extend from the reservoir 2 via tube 10 or plug 8 into either the upper or lower lacrimal duct terminating an endcap 6 that interfaces with a puncta lacrimalia (a punctum) wherein the plug may extend beyond the endcap 6 and interface with the tear film of the eye.
Figures 8A, 8B, 8C, 8D:
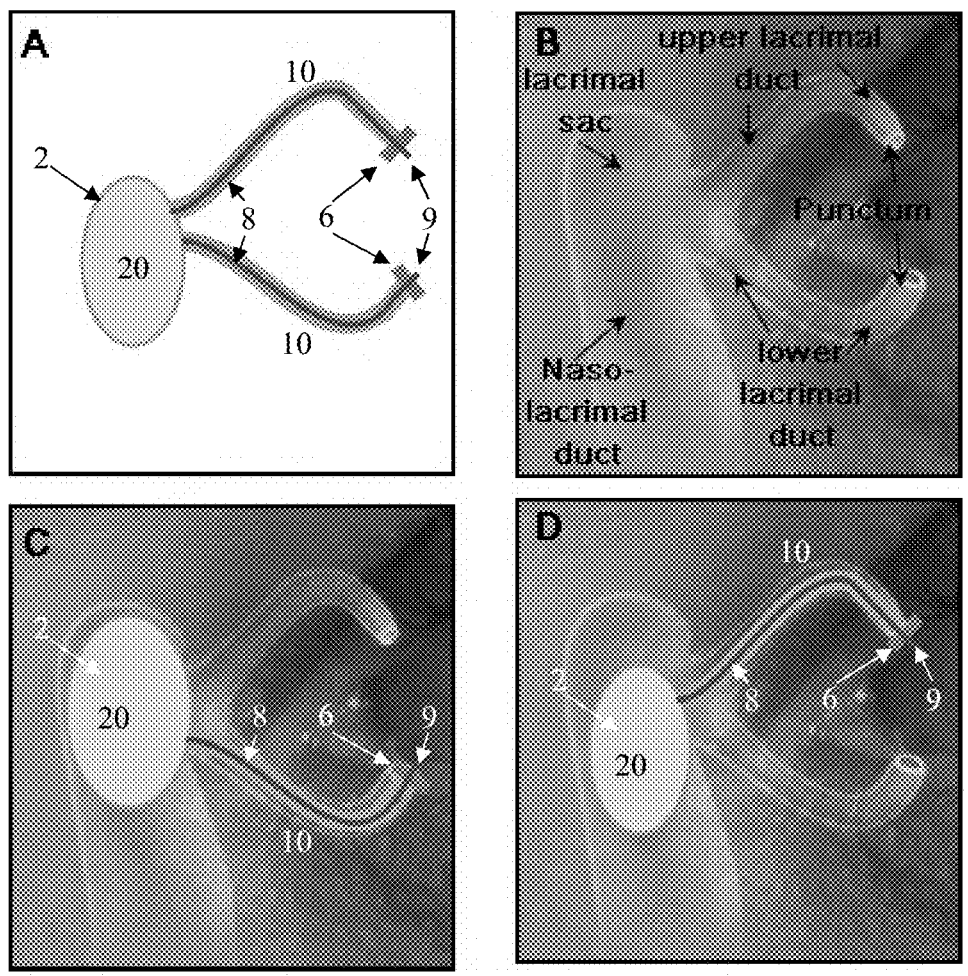
FIG. 8A-D shows examples of the filled reservoir balloon 2 with device/system properly inserted within the lacrimal system, portion of the lacrimal system, and the inflated device/system by itself.

Referring to FIG. 2 and FIG. 8, in one embodiment, the reservoir balloon 2 is implanted within the sinuses surrounding the eye. In one embodiment, the punctal endcap 6 or distal endcap 6 allows for filling the reservoir balloon 2 with medication wherein the plug 8 is removed. In one embodiment, the reservoir balloon 2 sits in a sinus and allows for delivery of drug through the connected tube 10 through said plug 8 from said reservoir balloon 2. In one embodiment, the punctal portion is implanted through the caruncle or through the conjunctiva (similar to implantation of a jones tube) and allow for the reservoir balloon 2 through the plug 8 to deliver drug directly to the tear film of the eye.

The device with associated reservoir balloon 2 can be implanted so that the distal endcap 6 has the plug 8 with the plug peak 9 extended from the port 7 of the endcap 6 is proximate to the tear film abutting the upper or lower punctum and the opposite end is composed of a reservoir balloon 2 (positioned in the lacrimal sac) that can be filled with an active ingredient, such as a drug or other therapeutic solution. Once filled, the active ingredient will be "wicked" from the reservoir balloon 2 from the exit port 3 through the connected tube 10 with lumen 11 and through the plug 8 to the distal opening port 7 in the endcap 6, which is proximate to the tear film. In one embodiment, said plug 8 comprises a flow-limiting rod. The drug may then enter the tear film and be absorbed by eye tissues to treat various ocular diseases. The device may or may not also connect to the nasal cavity through the termination of the tear duct system. The device may contain one or more egress tracks 13 connecting the endcap 6 to the lacrimal sac to allow for tear drainage away from the eye towards the natural lacrimal outflow system. In one embodiment, the endcap contains at least one additional port that connects at least one egress track 13 towards the reservoir balloon end of the device. In one embodiment, said egress track 13 terminates externally from said reservoir balloon 2 to enable drainage from the tear film of the eye to the lacrimal sac and beyond. The egress of drug 20 from the reservoir balloon 2 of the device may be entirely dependent on the nature of and positioning of the plug 8. In one embodiment, no active pumps are needed. In some embodiments, drugs 20 are delivered long term to the ocular surface in a regular and consistent manner. Other devices that deliver drug to the tear film using a punctal plug or lacrimal plug do so by a drug core that degrades after contact with the tear film.

While not limiting the current invention, one method of insertion of the device 1 would be to introduce the collapsed device on the punctal side in an insertion method similar to the introduction of a Crawford tube. In one embodiment, the collapsed device is introduced into the lacrimal system with an insertion catheter 19. The collapsed reservoir balloon 2 of the device is envisioned to fit through the punctum and canaliculus wherein the reservoir balloon 2 of the device would reside in the lacrimal sac allowing for expansion when filled with a therapeutic agent. In one embodiment, a lubricant is coupled with the system to allow for smoother atraumatic insertion. In one embodiment, the device further comprises a guide-wire 16 to enable delivery of said device into the lacrimal system. In the embodiment, the device contains a further tube 10 from the reservoir 2 allowing access to the reservoir 2 from the nasolacrimal duct for flushing and refilling. In one embodiment, a further tube could be accessed through various means including, but not limited to a small clip upon the tube, a groove in groove lock system, a kiss lock/coin purse system of closure, or complete closure or crimping of the end of the tube. While not limiting the device, it is envisioned that the device would conform the standard anatomical size variations. In one embodiment, the device could be used for subjects of various sizes and age ranges. In one embodiment, the device may not be appropriate in certain subjects, including, but not limited to subjects with trauma to the nasolacrimal system, subjects with chronic nasal inflammation, or dacryocystitis. Dacryocystitis is an inflammation of the nasolacrimal sac, frequently caused by nasolacrimal duct obstruction or infection. In one embodiment, the device functions and serves for at least two months or greater than sixty days. In the particular cases of treating dye eye or glaucoma, the device therapy would last at least two months. In the case of post-surgical treatment of conditions, such as cataracts, would involve treatment ranging of two to six week, possibly longer.

As discussed above, the present invention provides compositions, methods and devices relating to a lacrimal, eye, sinuses and/or periocular tissues system implant devices, which greatly increase their ability to deliver therapeutic agents consistently with a simple straightforward design and in larger quantities than is currently available. In one aspect, the present invention provides for the combination of various therapeutic agents and lacrimal, eye, sinuses and/or periocular tissues system implant for use in medical intervention, continuing medical therapy, and/or cosmetic or reconstructive surgery. In one aspect, the present invention is a lacrimal, eye, sinuses and/or periocular tissues system therapeutic agent delivery device for use in medical intervention, continuing medical therapy, and/or cosmetic or reconstructive surgery.

In some examples, an antimicrobial coating can be disposed on, or impregnated in, at least a portion of the outer surface of the implant body to further prevent microbial growth on the implant body. In an example, the antimicrobial coating can include an agent selected from the group comprising 2-bromo-2-nitropropane-1,3-diol, 5-bromo-5-nitro-1,3-dioxane, 7-ethyl bicyclooxazolidine, benzalkonium chloride, benzethonium chloride, benzoic acid, benzyl alcohol, boric acid, bronopol, cetylpyridinium chloride, chlorhexidine digluconate, chloroacetamide, chlorobutanol, chloromethyl isothiazolinone and methyl isothiazoline, dimethoxane, dimethyl oxazolidine, dimethyl hydroxymethyl pyrazole, chloroxylenol, dehydroacetic acid, diazolidinyl urea, dichlorobenzyl alcohol, DMDM hydantoin, ethyl alcohol, formaldehyde, glutaraldehyde, hexachlorophene, hexetidine, hexamethylenetramine, imidazolidinyl urea, iodopropynyl butylcarbamate, isothiazolinones, methenammonium chloride, methyldibromo glutaronitrile, MDM hydantoin, minocycline, ortho phenylphenol, p-chloro-m-cresol, parabens (butylparaben, ethylparaben, methylparaben), phenethyl alcohol, phenoxyethanol, piroctane olamine, polyaminopropyl biguanide, polymethoxy bicyclic oxazolidine, polyoxymethylene, polyquaternium-42, potassium benzoate, potassium sorbate, propionic acid, quaternium-15, rifampin, salicylic acid, selenium disulfide, sodium borate, sodium iodate, sodium hydroxymethylglycinate, sodium propionate, sodium pyrithione, sorbic acid, thimerosal, triclosan, triclocarban, undecylenic acid, zinc phenosulfonate, and zinc pyrithione. In an example, the antimicrobial coating can include a material selected from the group comprising silver lactate, silver phosphate, silver citrate, silver acetate, silver benzoate, silver chloride, silver iodide, silver iodate, silver nitrate, silver sulfadiazine, silver palmitate or one or more mixtures thereof. In an example, the antimicrobial coating can include at least one of an antibiotic or an antiseptic. For instance, the antimicrobial coating can include a temporary anesthetic lasting, on average, between a few hours and a day. In still other examples, the antimicrobial coating can include a drug use to treat an underlying disease, such as a bolus for immediate effect.

A therapeutic agent (or simply "agent") can comprise, among other things, a drug made from one or any combination of the following or their equivalents, derivatives or analogs, including, anti-glaucoma medications, (e.g. adrenergic agonists, adrenergic antagonists (beta blockers), carbonic anhydrase inhibitors (CAIs, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID or other analgesic and pain management compounds), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic, mydriatic or the like.

Example available agents include, but are not limited to, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Examples of such anti-inflammatory steroids contemplated for use with the present lacrimal implants, include triamcinolone acetonide (generic name) and corticosteroids that include, for example, triamcinolone, dexamethasone, fluocinolone, cortisone, prednisolone, flumetholone, and derivatives thereof); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil; immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandins, prostaglandin precursors, including antiglaucoma drugs including beta-blockers such as Timolol, betaxolol, levobunolol, atenolol, and prostaglandin analogues such as bimatoprost, travoprost, latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

Additional agents that can be used with the present lacrimal implants include, but are not limited to, drugs that have been approved under Section 505 of the United States Federal Food, Drug, and Cosmetic Act or under the Public Health Service Act. The present lacrimal implants can also be used with drugs listed in the FDA Orange Book that has or records the same date as, earlier date than, or later date than, the filing date of this patent document. For example, these drugs can include but are not limited to, among others, dorzolamide, olopatadine, travoprost, bimatoprost, cyclosporin, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, suprofenac, binoxan, patanol, dexamethasone/tobramycin combination, moxifloxacin, or acyclovir.

Examples of diseases or disorders that can be treated with above-listed agents include, but are not limited to, glaucoma, pre- and post-surgical ocular treatments, dry eye, anti-eye allergy, anti-infective, post-surgical inflammation or pain, or respiration-related disorders, such as allergies In some examples, the therapeutic agent can include a lubricant or a surfactant, for example a lubricant to treat dry eye. In other examples, the therapeutic agent can include an absorbent capable of absorbing tear from an eye.

Although the form of the therapeutic agent is envisioned to be a fluid 20 with a flow-limited release through an exit port 3 connected to the reservoir 2, is also possible that the drug supply can comprise one or more biocompatible materials capable of providing a sustained release of the one or more agents. For example, a biodegradable matrix, a porous drug supply, or liquid drugs supply. A matrix that includes the agents can be formed from either biodegradable or non-biodegradable polymers. In some examples, a non-biodegradable drug supply can include, but are not limited to, silicone, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, Ill.; CONICHROME® from Carpenter Metals Corp., Wyomissing, Pa.). In some examples, a biodegradable drug supply can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some examples, the drug supply can comprise a hydrogel polymer. Any drug supply matrix must be capable of compression-controlled release through the previously described port.

Thus, specific compositions and methods of lacrimal system for drug delivery have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently continued.

REFERENCES

1. Fleisher, D. et al. (1996) "Improved Oral Drug Delivery: Solubility Limitations Overcome by the Use of Prodrugs," *Adv. Drug Delivery Rev.* 19(2), 115-130.
2. Smith, C. D. et al. (1994) "A Sensitive Assay for Taxol and Other Microtubule-Stabilizing Agents," *Cancer Lett.* 79(2), 213-219.
3. Mooberry, S. L. et al. (1995) "Tubercidin Stabilizes Microtubules against Vinblastine-Induced Depolymerization, a Taxol-Like Effect," *Cancer Lett.* 96(2), 261-266.
4. Ro, A. J. et al. (2012) "Morphological and Degradation Studies of Sirolimus-Containing Poly(Lactide-Co-Glycolide) Discs," *Journal of Biomedical Materials Research Part B: Applied Biomaterials* 100B(3), 767-777.
5. Sim, S. et al. "Composite Lacrimal Insert and Related Methods," United States Patent Application Publication Number US 2010-0034870 A1, application Ser. No. 12/432,553, filed Apr. 29, 2009. (published Feb. 11, 2010).
6. Hubbell, J. A. et al. "Photopolymerizable Biodegradable Hydrogels as Tissue Contacting Materials and Controlled-Release Carriers," U.S. Pat. No. 5,410,016, application Ser. No. 08/022,687, filed Mar. 1, 1993. (issued Apr. 25, 1995).
7. Rodstrom, T. R. et al. "Punctal Plugs and Methods of Delivering Therapeutic Agents," United States Patent Application Publication Number US 2008-0181930 A1, application Ser. No. 12/022,520, filed Jan. 30, 2008. (published Jul. 31, 2008).
8. Borgia, M. J. et al. "Punctal Plugs for the Delivery of Active Agents," United States Patent Application Publication Number US 2007-0298075 A1, application Ser. No. 11/759,327, filed Jun. 7, 2007. (published Dec. 27, 2007).
9. Brubaker, M. J. et al. "Sustained Release Drug Delivery Devices," WIPO PCT Patent Publication Number WO/2002/056863, Application PCT/US2001/048804, filed Jul. 25, 2002. (published Dec. 17, 2001).
10. Rapacki, A. R. et al. "Lacrimal Implants and Related Methods," United States Patent Application Publication Number US 2010-0274204 A1, application Ser. No. 12/710,855, filed Feb. 23, 2010. (published Oct. 28, 2010).
11. Cohan, B. E. "Opthalmic Insert and Method for Sustained Release of Medication to the Eye," European Patent EP1891942B1, Application EP1178779A1, filed Apr. 7, 2000. (issued Mar. 3, 2010).
12. Murube, J. et al. (2003) "Subcutaneous Abdominal Artificial Tears Pump-Reservoir for Severe Dry Eyes," *Orbit* 22(1), 29.
13. Freilich, D. "Ophthalmic Insert," United States Patent Application Publication Number US 2008-0086101 A1, application Ser. No. 11/641,903, filed Dec. 20, 2006. (published Apr. 10, 2008).
14. Cohan, B. E. and Diamond, H. "Ophthalmic Insert and Method for Sustained Release of Medication to the Eye," U.S. Pat. No. 6,196,993, application Ser. No. 09/294,720, filed Apr. 19, 1999. (issued Mar. 6, 2001).

What is claimed:

1. A lacrimal system for drug delivery to an eye, comprising;
    a) a reservoir balloon having an exit port, the reservoir balloon configured to enclose a volume of fluid;
    b) a tube comprising at least a first lumen and a second lumen, a first end, and a second end; wherein the first end of the tube is fluidly coupled to the exit port of the reservoir balloon; wherein the at least the first lumen and the second lumen each extend through the first end of the tube such that the at least the first lumen and the second lumen are each in fluid communication with the reservoir balloon;

c) an endcap comprising a port and configured to interface with a punctum and to be in contact with a tear film of the eye of a subject during use to facilitate delivery of fluid from the reservoir balloon to the eye, wherein the endcap is fluidly coupled to the second end of the tube;

d) a flow-limiting plug, the flow-limiting plug at least partially residing within the at least the first lumen of the tube and extending through the port of the endcap to provide flow resistance and create a pressure differential to at least partially control a flow of the fluid from the reservoir balloon, through the at least the first lumen, to the eye during use, wherein the flow-limiting plug comprises a hydrogel; and e) a guide-wire.

2. The lacrimal system of claim 1, wherein the fluid comprises at least one active agent.

3. The lacrimal system of claim 2, wherein the flow-limiting plug absorbs fluid from the reservoir balloon and delivers fluid through the at least the first lumen to thereby affect a rate of the flow of fluid from the reservoir balloon to the eye during use.

4. The lacrimal system of claim 2, wherein the at least one active agent comprises at least one of an anti-glaucoma agent, an antimicrobial agent, an anti-inflammatory agent, a decongestant, an agent that prevents or modifies an allergic response, a mast cell stabilizer, a cycloplegic or mydriatic agent.

5. The lacrimal system of claim 1, wherein the lacrimal system further comprises at least one egress track connecting the endcap to an outside of the reservoir balloon.

6. The lacrimal system of claim 1, wherein the flow-limiting plug occludes the at least the first lumen.

7. The lacrimal system of claim 1, wherein the hydrogel of the flow-limiting plug comprises silicone.

8. The lacrimal system of claim 1, wherein the tube comprises medical grade silicone.

9. The lacrimal system of claim 1, wherein the tube is flexible.

10. The lacrimal system of claim 1, wherein the reservoir balloon enables anatomical fixation during use.

11. The lacrimal system of claim 1, wherein the lacrimal system further comprises a lubricant.

12. The lacrimal system of claim 1, wherein the guide-wire configured to be removably coupled to the second lumen enables delivery of the lacrimal system for drug delivery to the eye.

13. The lacrimal system of claim 1, wherein the flow-limiting plug extends between 1 to 200 microns beyond a surface of the endcap to facilitate direct contact with the tear film of the eye.

14. The lacrimal system of claim 1, wherein the tube is configured to extend from a lacrimal sac of the eye to the endcap.

15. The lacrimal system of claim 1, wherein the flow-limiting plug extends from the reservoir balloon to the endcap.

16. The lacrimal system of claim 1, wherein the guide-wire comprises an open lumen.

17. The lacrimal system of claim 1, wherein the reservoir balloon is substantially elastic.

18. The lacrimal system of claim 1, wherein the hydrogel is configured to absorb at least a portion of the fluid from the reservoir balloon.

19. The lacrimal system of claim 1, wherein the reservoir balloon is configured to provide a pressure to the volume of the fluid to at least partially cause the flow of the fluid.

20. The lacrimal system of claim 1, wherein the second lumen extends through the endcap at the second end of the tube.

21. The lacrimal system of claim 1, wherein the at least the first lumen is in fluid communication with the port.

22. A method for delivering a composition comprising at least one active agent to an eye of a subject, the method comprising:

inserting the lacrimal system for drug delivery of claim 1 into the eye of the subject;

filling the reservoir balloon of the lacrimal system for drug delivery with the composition; and administering the composition to the eye of the subject.

* * * * *